US011497622B2

(12) United States Patent
Jimenez et al.

(10) Patent No.: US 11,497,622 B2
(45) Date of Patent: Nov. 15, 2022

(54) TRANSVERSELY EXPANDABLE MINIMALLY INVASIVE INTERVERTEBRAL CAGE AND INSERTION AND EXTRACTION DEVICE

(71) Applicant: Octagon Spine LLC, Seattle, WA (US)

(72) Inventors: Omar F. Jimenez, Seattle, WA (US); Yefim I. Safris, Golden Valley, MN (US)

(73) Assignee: Ex Technology, LLC, Seattle, WA (US)

( * ) Notice: Subject to any disclaimer, the term of this patent is extended or adjusted under 35 U.S.C. 154(b) by 210 days.

(21) Appl. No.: 16/574,265

(22) Filed: Sep. 18, 2019

(65) Prior Publication Data

US 2020/0281743 A1    Sep. 10, 2020

Related U.S. Application Data

(63) Continuation-in-part of application No. 16/292,565, filed on Mar. 5, 2019, now Pat. No. 11,234,835.

(51) Int. Cl.
| | |
|---|---|
| *A61F 2/46* | (2006.01) |
| *A61F 2/44* | (2006.01) |
| *A61F 2/30* | (2006.01) |

(52) U.S. Cl.
CPC ............ *A61F 2/4611* (2013.01); *A61F 2/447* (2013.01); *A61F 2/4603* (2013.01); (Continued)

(58) Field of Classification Search
CPC ...... A61F 2/4611; A61F 2/447; A61F 2/4465; A61F 2002/30579
See application file for complete search history.

(56) References Cited

U.S. PATENT DOCUMENTS

| 283,218 A | 8/1883 | Rycke |
|---|---|---|
| 703,251 A | 6/1902 | Haire |
| (Continued) | | |

FOREIGN PATENT DOCUMENTS

| EP | 1342456 A1 | 9/2003 |
|---|---|---|
| EP | 1552797 A2 | 7/2005 |
| (Continued) | | |

OTHER PUBLICATIONS

PCT/US2010/042941, filed Jul. 22, 2010, International Search Report and Written Opinion, dated Apr. 25, 2011.
(Continued)

*Primary Examiner* — Julianna N Harvey
(74) *Attorney, Agent, or Firm* — Patterson Thuente Pedersen, P.A.

(57) ABSTRACT

Disclosed herein are systems and methods for intervertebral body fusion that provide more robust support within the disc space. Intervertebral body fusion devices can have a unitary monolithic body including a plurality of body segments interconnected with each other by flexure members. Devices can be configured to be inserted through an opening in a compressed configuration and then expanded within the disc space to an expanded configuration. In the expanded configuration, devices can have a greater mediolateral or transverse to the disc space footprint. This wider footprint provides greater support for the vertebrae relative to the size of the opening through which the device is inserted. Insertion devices for inserting, expanding and extracting such implants are also disclosed.

20 Claims, 27 Drawing Sheets

(52) U.S. Cl.
CPC .............. *A61F 2002/30143* (2013.01); *A61F 2002/30579* (2013.01); *A61F 2002/30593* (2013.01); *A61F 2002/30622* (2013.01); *A61F 2002/4627* (2013.01)

(56) References Cited

U.S. PATENT DOCUMENTS

| | | | |
|---|---|---|---|
| 811,344 A | 1/1906 | Wands |
| 1,388,836 A | 8/1921 | Ripsch et al. |
| 1,500,859 A | 7/1924 | Wright |
| 1,547,946 A | 7/1925 | Myers |
| 2,106,088 A | 1/1938 | De Tar |
| 2,231,221 A | 2/1941 | Rector |
| 2,453,656 A | 11/1948 | Bullard, III |
| 2,666,334 A | 1/1954 | Nalle |
| 2,711,105 A | 6/1955 | Williams |
| 2,842,976 A | 7/1958 | Young |
| 2,891,408 A | 6/1959 | Burt, Jr. |
| 3,386,128 A | 6/1968 | Vyvyan |
| 3,449,971 A | 6/1969 | Posh |
| 3,575,475 A | 4/1971 | Boerner |
| 3,596,863 A | 8/1971 | Kaspareck |
| 3,597,938 A | 8/1971 | Hellen |
| 3,700,289 A | 10/1972 | Bilinski et al. |
| 3,700,290 A | 10/1972 | Ensinger |
| 3,708,925 A | 1/1973 | Ainoura |
| 3,709,132 A | 1/1973 | Farrell et al. |
| 3,916,596 A | 11/1975 | Hawley |
| 3,985,000 A | 10/1976 | Hartz |
| 3,988,906 A | 11/1976 | Smith |
| 4,261,211 A | 4/1981 | Haberland |
| 4,396,047 A | 8/1983 | Balkus |
| 4,478,109 A | 10/1984 | Kobelt |
| 4,516,303 A | 5/1985 | Kloster |
| 4,528,864 A | 7/1985 | Craig |
| 4,559,717 A | 12/1985 | Scire et al. |
| 4,630,495 A | 12/1986 | Smith |
| 4,691,586 A | 9/1987 | van Leijenhorst et al. |
| 4,694,703 A | 9/1987 | Routson |
| 4,869,552 A | 9/1989 | Tolleson et al. |
| 5,133,108 A | 7/1992 | Esnault |
| 5,172,442 A | 12/1992 | Bartley et al. |
| 5,181,371 A | 1/1993 | Deworth |
| 5,196,857 A | 3/1993 | Chiappetta et al. |
| 5,198,932 A | 3/1993 | Takamura |
| 5,222,986 A | 6/1993 | Wright |
| 5,313,852 A | 5/1994 | Arena |
| 5,374,556 A | 12/1994 | Bennett et al. |
| 5,439,377 A | 8/1995 | Milanovich |
| 5,445,471 A | 8/1995 | Wexler et al. |
| 5,554,191 A | 9/1996 | Lahille et al. |
| 5,645,599 A | 7/1997 | Samani |
| 5,653,763 A | 8/1997 | Errico et al. |
| 5,664,457 A | 9/1997 | Nejati |
| 5,904,479 A | 5/1999 | Staples |
| 5,960,670 A | 10/1999 | Iverson et al. |
| 5,980,252 A | 11/1999 | Samchukov et al. |
| 5,988,006 A | 11/1999 | Fleytman |
| 6,039,761 A | 3/2000 | Li et al. |
| 6,045,579 A | 4/2000 | Hochshuler et al. |
| 6,056,491 A | 5/2000 | Hsu |
| 6,080,193 A | 6/2000 | Hochshuler et al. |
| 6,136,031 A | 10/2000 | Middleton |
| 6,175,989 B1 | 1/2001 | Carpentar et al. |
| 6,315,797 B1 | 11/2001 | Middleton |
| 6,350,317 B1 | 2/2002 | Hao et al. |
| 6,378,172 B1 | 4/2002 | Schrage |
| 6,395,035 B2 | 5/2002 | Bresina et al. |
| 6,454,806 B1 | 9/2002 | Cohen et al. |
| 6,454,807 B1 | 9/2002 | Jackson |
| 6,484,608 B1 | 11/2002 | Ziavras |
| 6,517,772 B1 | 2/2003 | Woolf |
| 6,554,526 B1 | 4/2003 | Egelandsdal |
| 6,616,695 B1 | 9/2003 | Crozet et al. |
| 6,641,614 B1 | 11/2003 | Wagner et al. |
| 6,719,796 B2 | 4/2004 | Cohen et al. |
| 6,752,832 B2 | 6/2004 | Neumann |
| 6,772,479 B2 | 8/2004 | Hinkley et al. |
| 6,802,229 B1 | 10/2004 | Lambert |
| 6,808,537 B2 | 10/2004 | Michelson |
| 6,863,673 B2 | 3/2005 | Gerbec et al. |
| 6,932,844 B2 | 8/2005 | Ralph et al. |
| 6,953,477 B2 | 10/2005 | Berry |
| 7,018,415 B1 | 3/2006 | McKay |
| 7,051,610 B2 | 5/2006 | Stoianovici et al. |
| 7,070,598 B2 | 7/2006 | Lim et al. |
| 7,087,055 B2 | 8/2006 | Lim et al. |
| 7,201,751 B2 | 4/2007 | Zucherman et al. |
| 7,273,373 B2 | 9/2007 | Horiuchi |
| 7,308,747 B2 | 12/2007 | Smith et al. |
| 7,316,381 B2 | 1/2008 | Häcker et al. |
| 7,410,201 B1 | 8/2008 | Wilson et al. |
| 7,425,103 B2 | 9/2008 | Perez-Sanchez |
| 7,431,735 B2 | 10/2008 | Liu et al. |
| 7,435,032 B1 | 10/2008 | Murphey et al. |
| 7,547,325 B2 | 6/2009 | Biedermann et al. |
| 7,584,682 B2 | 9/2009 | Hsiao |
| 7,611,538 B2 | 11/2009 | Belliard et al. |
| 7,632,281 B2 | 12/2009 | Errico et al. |
| 7,674,296 B2 | 3/2010 | Rhoda et al. |
| 7,682,376 B2 | 3/2010 | Trieu |
| 7,708,779 B2 | 5/2010 | Edie et al. |
| 7,712,389 B2 | 5/2010 | Wang |
| 7,753,958 B2 | 7/2010 | Gordon et al. |
| 7,758,645 B2 | 7/2010 | Studer |
| 7,758,648 B2 | 7/2010 | Castleman et al. |
| 7,892,285 B2 | 2/2011 | Viker |
| 7,896,919 B2 | 3/2011 | Belliard et al. |
| 7,901,409 B2 | 3/2011 | Canaveral et al. |
| 7,947,078 B2 | 5/2011 | Siegal |
| 7,951,199 B2 | 5/2011 | Miller |
| 7,985,256 B2 | 7/2011 | Grotz et al. |
| 8,057,549 B2 | 11/2011 | Butterman et al. |
| 8,070,813 B2 | 12/2011 | Grotz et al. |
| 8,088,163 B1 | 1/2012 | Kleiner |
| 8,192,495 B2 | 6/2012 | Simpson et al. |
| 8,303,663 B2 | 11/2012 | Jimenez et al. |
| 8,496,706 B2 | 7/2013 | Ragab et al. |
| 8,523,944 B2 | 9/2013 | Jimenez et al. |
| 8,540,452 B2 | 9/2013 | Jimenez et al. |
| 8,628,577 B1 | 1/2014 | Jimenez |
| 8,636,746 B2 | 1/2014 | Jimenez et al. |
| 8,771,360 B2 | 7/2014 | Jimenez et al. |
| 8,795,366 B2 | 8/2014 | Varela |
| 8,894,712 B2 | 11/2014 | Varela |
| 8,906,100 B2 | 12/2014 | Jimenez |
| 8,932,302 B2 | 1/2015 | Jimenez et al. |
| 8,940,049 B1 | 1/2015 | Jimenez et al. |
| 9,358,125 B2 | 6/2016 | Jimenez et al. |
| 9,381,092 B2 | 7/2016 | Jimenez et al. |
| 9,445,917 B2 | 9/2016 | Jimenez et al. |
| 9,445,918 B1 * | 9/2016 | Lin ................... A61F 2/4684 |
| 9,474,621 B2 | 10/2016 | Jimenez |
| 9,486,328 B2 | 11/2016 | Jimenez |
| 9,498,270 B2 | 11/2016 | Jimenez |
| 9,668,879 B2 | 6/2017 | Jimenez et al. |
| 9,867,717 B2 | 1/2018 | Jimenez |
| 10,060,469 B2 | 8/2018 | Jimenez et al. |
| 2002/0128716 A1 | 9/2002 | Cohen et al. |
| 2002/0138146 A1 | 9/2002 | Jackson |
| 2002/0177897 A1 * | 11/2002 | Michelson ............... A61F 2/44 623/17.11 |
| 2003/0077110 A1 | 4/2003 | Knowles |
| 2003/0233145 A1 | 12/2003 | Landry et al. |
| 2004/0049271 A1 | 3/2004 | Biedermann et al. |
| 2004/0111157 A1 | 6/2004 | Ralph et al. |
| 2004/0153156 A1 | 8/2004 | Cohen et al. |
| 2004/0193158 A1 | 9/2004 | Lim |
| 2004/0225364 A1 | 11/2004 | Richelsoph et al. |
| 2005/0000228 A1 | 1/2005 | De Sousa et al. |
| 2005/0033431 A1 | 2/2005 | Gordon et al. |
| 2005/0095384 A1 | 5/2005 | Wittmeyer, Jr. |
| 2005/0113921 A1 | 5/2005 | An et al. |
| 2005/0113924 A1 | 5/2005 | Buttermann |

(56) References Cited

U.S. PATENT DOCUMENTS

| | | |
|---|---|---|
| 2005/0175406 A1 | 8/2005 | Perez-Sanchez |
| 2005/0182416 A1 | 8/2005 | Lim et al. |
| 2005/0261769 A1 | 11/2005 | Moskowitz et al. |
| 2006/0004447 A1 | 1/2006 | Mastrorio et al. |
| 2006/0004455 A1 | 1/2006 | Leonard et al. |
| 2006/0025862 A1 | 2/2006 | Villiers et al. |
| 2006/0058878 A1 | 3/2006 | Michelson |
| 2006/0129244 A1 | 6/2006 | Ensign |
| 2006/0149385 A1 | 7/2006 | McKay |
| 2006/0184171 A1 | 8/2006 | Biedermann et al. |
| 2006/0247781 A1 | 11/2006 | Francis |
| 2006/0253201 A1 | 11/2006 | McLuen |
| 2006/0293752 A1 | 12/2006 | Mounmene et al. |
| 2007/0032791 A1 | 2/2007 | Greenhalgh et al. |
| 2007/0049943 A1 | 3/2007 | Moskowitz et al. |
| 2007/0083267 A1 | 4/2007 | Miz et al. |
| 2007/0093901 A1 | 4/2007 | Grotz et al. |
| 2007/0129730 A1 | 6/2007 | Woods et al. |
| 2007/0173826 A1 | 7/2007 | Canaveral |
| 2007/0185577 A1 | 8/2007 | Malek |
| 2007/0191954 A1 | 8/2007 | Hansell et al. |
| 2007/0191958 A1 | 8/2007 | Abdou |
| 2007/0198089 A1 | 8/2007 | Moskowitz et al. |
| 2007/0219634 A1 | 9/2007 | Greenhalgh et al. |
| 2007/0222100 A1 | 9/2007 | Husted et al. |
| 2007/0225726 A1* | 9/2007 | Dye .................. A61F 2/4465 606/99 |
| 2007/0250171 A1 | 10/2007 | Bonin, Jr. |
| 2007/0255415 A1 | 11/2007 | Edie et al. |
| 2007/0282449 A1 | 12/2007 | de Villiers et al. |
| 2007/0288092 A1 | 12/2007 | Bambakidis |
| 2007/0293329 A1 | 12/2007 | Glimpel et al. |
| 2007/0293948 A1 | 12/2007 | Bagga et al. |
| 2008/0026903 A1 | 1/2008 | Flugrad et al. |
| 2008/0077246 A1 | 3/2008 | Fehling et al. |
| 2008/0091211 A1 | 4/2008 | Gately |
| 2008/0100179 A1 | 5/2008 | Ruggeri et al. |
| 2008/0103601 A1 | 5/2008 | Biro et al. |
| 2008/0114367 A1 | 5/2008 | Meyer |
| 2008/0140207 A1 | 6/2008 | Olmos |
| 2008/0147194 A1 | 6/2008 | Grotz et al. |
| 2008/0154266 A1 | 6/2008 | Protopsaltis et al. |
| 2008/0161920 A1 | 7/2008 | Melkent |
| 2008/0161931 A1 | 7/2008 | Perez-Cruet et al. |
| 2008/0168855 A1 | 7/2008 | Giefer et al. |
| 2008/0183204 A1 | 7/2008 | Greenhalgh et al. |
| 2008/0188941 A1 | 8/2008 | Grotz |
| 2008/0210039 A1 | 9/2008 | Brun |
| 2008/0221694 A1 | 9/2008 | Warnick et al. |
| 2008/0234736 A1 | 9/2008 | Trieu et al. |
| 2008/0243255 A1 | 10/2008 | Butler et al. |
| 2008/0281423 A1 | 11/2008 | Sheffer et al. |
| 2008/0292392 A1 | 11/2008 | Voellmer |
| 2008/0319487 A1 | 12/2008 | Fielding et al. |
| 2009/0012564 A1 | 1/2009 | Chirico et al. |
| 2009/0076614 A1 | 3/2009 | Arramon |
| 2009/0099568 A1 | 4/2009 | Lowry et al. |
| 2009/0164017 A1 | 6/2009 | Sommerich et al. |
| 2009/0210061 A1 | 8/2009 | Sledge |
| 2009/0222100 A1 | 9/2009 | Cipoletti et al. |
| 2009/0234362 A1 | 9/2009 | Blain et al. |
| 2009/0259316 A1 | 10/2009 | Ginn et al. |
| 2009/0299478 A1 | 12/2009 | Carls et al. |
| 2009/0306672 A1 | 12/2009 | Reindel et al. |
| 2010/0004688 A1 | 1/2010 | Maas et al. |
| 2010/0076557 A1 | 3/2010 | Miller |
| 2010/0082109 A1 | 4/2010 | Greenhalgh et al. |
| 2010/0094305 A1 | 4/2010 | Chang et al. |
| 2010/0161062 A1 | 6/2010 | Foley et al. |
| 2010/0185291 A1 | 7/2010 | Jimenez et al. |
| 2010/0192715 A1 | 8/2010 | Vauchel et al. |
| 2010/0209184 A1 | 8/2010 | Jimenez et al. |
| 2011/0015638 A1 | 1/2011 | Pischl et al. |
| 2011/0054616 A1 | 3/2011 | Kamran et al. |
| 2011/0093075 A1 | 4/2011 | Duplessis et al. |
| 2011/0112644 A1 | 5/2011 | Zilberstein et al. |
| 2011/0138948 A1 | 6/2011 | Jimenez et al. |
| 2011/0160861 A1 | 6/2011 | Jimenez et al. |
| 2011/0172774 A1 | 7/2011 | Varela |
| 2011/0270398 A1 | 11/2011 | Grotz et al. |
| 2012/0010653 A1 | 1/2012 | Seifert et al. |
| 2012/0029636 A1 | 2/2012 | Ragab et al. |
| 2012/0083887 A1 | 4/2012 | Purcell et al. |
| 2012/0116518 A1 | 5/2012 | Grotz et al. |
| 2012/0158071 A1 | 6/2012 | Jimenez et al. |
| 2012/0185049 A1 | 7/2012 | Varela |
| 2012/0226357 A1 | 9/2012 | Varela |
| 2012/0271419 A1 | 10/2012 | Marik |
| 2012/0290094 A1 | 11/2012 | Lim et al. |
| 2012/0303124 A1 | 11/2012 | McLuen et al. |
| 2012/0323329 A1 | 12/2012 | Jimenez et al. |
| 2013/0053966 A1 | 2/2013 | Jimenez et al. |
| 2013/0144388 A1 | 6/2013 | Emery et al. |
| 2013/0158664 A1 | 6/2013 | Palmatier et al. |
| 2013/0197642 A1 | 8/2013 | Ernst |
| 2013/0317615 A1 | 11/2013 | Jimenez et al. |
| 2014/0012383 A1 | 1/2014 | Triplett et al. |
| 2014/0018924 A1 | 1/2014 | McManus et al. |
| 2014/0039622 A1 | 2/2014 | Glerum et al. |
| 2014/0058512 A1 | 2/2014 | Petersheim |
| 2014/0088714 A1 | 3/2014 | Miller et al. |
| 2014/0140757 A1 | 5/2014 | Jimenez et al. |
| 2014/0156007 A1 | 6/2014 | Pabst et al. |
| 2014/0194991 A1 | 7/2014 | Jimenez |
| 2014/0236296 A1 | 8/2014 | Wagner et al. |
| 2014/0249629 A1 | 9/2014 | Moskowitz et al. |
| 2014/0277490 A1 | 9/2014 | Perloff et al. |
| 2014/0343608 A1 | 11/2014 | Whiton et al. |
| 2015/0018951 A1 | 1/2015 | Leobl |
| 2015/0088258 A1 | 3/2015 | Jimenez et al. |
| 2015/0100128 A1 | 4/2015 | Glerum et al. |
| 2015/0148908 A1 | 5/2015 | Marino et al. |
| 2015/0230929 A1 | 8/2015 | Lorio |
| 2015/0272743 A1 | 10/2015 | Jimenez et al. |
| 2015/0272745 A1 | 10/2015 | Jimenez et al. |
| 2015/0272746 A1 | 10/2015 | Jimenez et al. |
| 2015/0351925 A1 | 12/2015 | Emerick et al. |
| 2016/0262907 A1 | 9/2016 | Jimenez |
| 2016/0356368 A1 | 12/2016 | Jimenez et al. |
| 2017/0056200 A1 | 3/2017 | Koch et al. |
| 2018/0021149 A1* | 1/2018 | Boehm .................. A61F 2/4611 606/99 |

FOREIGN PATENT DOCUMENTS

| | | |
|---|---|---|
| EP | 1881209 A1 | 1/2008 |
| FR | 2372998 A1 | 12/1976 |
| JP | 05-81194 | 4/1993 |
| JP | 2004-301135 A | 10/2004 |
| JP | 2008-208932 A | 9/2008 |
| WO | WO 2004/026188 A2 | 4/2004 |
| WO | WO 2004/109155 A1 | 12/2004 |
| WO | WO 2005/081330 A2 | 9/2005 |
| WO | WO 2005/096975 A2 | 10/2005 |
| WO | WO 2006/094535 A1 | 9/2006 |
| WO | WO 2006/116052 A2 | 11/2006 |
| WO | WO 2006/125329 A1 | 11/2006 |
| WO | WO 2007/002583 A2 | 1/2007 |
| WO | WO 2007/009107 A2 | 1/2007 |
| WO | WO 2007/028140 A2 | 3/2007 |
| WO | WO 2007/076377 A2 | 7/2007 |
| WO | WO 2007/111979 A2 | 10/2007 |
| WO | WO 2008/137192 A1 | 11/2008 |
| WO | WO 2009/018349 A2 | 2/2009 |
| WO | WO 2010/078468 A2 | 7/2010 |
| WO | WO 2010/078520 A2 | 7/2010 |
| WO | WO 2011/011609 A2 | 1/2011 |

(56) References Cited

FOREIGN PATENT DOCUMENTS

| WO | WO 2011/011626 A2 | 1/2011 |
|----|-------------------|--------|
| WO | WO 2014/066890 A1 | 5/2014 |

OTHER PUBLICATIONS

PCT/US2010/042915, filed Jul. 22, 2010, Search Report and Written Opinion dated Apr. 22, 2011.
PCT/US2009/069876, filed Dec. 30, 2009, International Search Report and Written Opinion dated Sep. 27, 2010, 10 pages.
PCT/US2009/069958, filed Dec. 31, 2009, International Search Report and Written Opinion dated Nov. 29, 2010, 7 pages.
PCT/US2015/055449, filed Oct. 14, 2015, International Search Report and Written Opinion dated Dec. 11, 2015, 9 pages.
PCT/US2015/032977, filed May 28, 2015, International Search Report and Written Opinion dated Sep. 21, 2015, 10 pages.
European Application No. EP 09837185.9, European Search Report dated May 14, 2013, 7 pages.
Japanese Application No. 2012-521784, JP Office Action dated Feb. 18, 2014, 8 pages.
PCT/US2013/067070, PCT Written Opinion/Search Report dated Feb. 27, 2014, 14 pages.
PCT/US2014/052913, PCT Written Opinion/Search Report dated Dec. 22, 2014, 10 pages.
European Application No. EP 10802916.6, Examination Report dated May 12, 2016, 4 pages.
Canadian Application No. 2,768,867, Office Action dated Aug. 4, 2016, 4 pages.
Canadian Application No. 2,768,867, Office Action dated Apr. 19, 2017, 4 pages.
European Application No. EP14887838.2, Extended European Search Report, dated Oct. 25, 2017, 8 pages.
Wenzel Spine, Inc., VariLift®-L Expandable Interbody Fusion Device: A proven solution for stand-alone fusion, Product Overview, 12 pages, 2010.
Peter A. Halverson, et. al., Tension-based Multi-stable Compliant: Rolling-contact Elements, Department of Mechanical Engineering, Brigham Young University, Provo UT, USA 84602, 34 pages, 2007.
Just L. Herder, Force Directed Design of Laparoscopic Forceps, ASME Design Engineering Technical Conference, 8 pages, 1998.
Alexander H. Slocum, Fundamentals of Design, 2005.
W. Küsswetter, A Supplementary Instrumentation for Posterior Fusion of Spine in Scoliosis, Archives of Orthopedic Traumatic Surgery, 1980, 1 page.
Chou et al., Efficacy of Anterior Cervical Fusion: Comparison of Titanium Cages, polyetheretherketone (PEEK) cages and autogenous bone grafts, Journal of Clinical Neuroscience, 2008, pp. 1240-1245.
Amelie Jeanneau, et. al., A Compliant Rolling Contact Joint and its Application in a 3-DOF Planar Parallel Mechanism with Kinematic Analysis, ASME, Design Engineering Technical Conferences, 9 pages, 2004.
Hunter et al., Overview of Medical Devices, Department of Radiology, University of Arizona, Aug. 2001, pp. 89-140, vol. 30, No. 4, ISSN: 0363-0188.
Medtronic Sofamor Danek USA, Inc., CAPSTONE Instrument Set Technique, http://www.mtortho.com/public/capstone.pdf, © 2005, 25 pages.
Medtronic, Capstone Peek Spinal System Surgical Technique, http://www.mtortho.com/public/capstone_peek_st.pdf, © 2009, 36 pages.
Website printout from https://seelio.com/w/fgf/omnilif-the-new-standard-in-spinal-deformity-correction-and-fusion?student=lumbarjax; dated Nov. 27, 2014, 5 pages.
Printout from Video for OmniLIF Anterior Insertion Approach from Lumber Jax; https://seelio.com/w/fgf/omnilif-the-new-standard-in-spinal-deformity-correction-and-fusion?student=lumbarjax; dated Nov. 27, 2014, 7 pages.
Printout from Video for OmniLIF Features from Lumber Jax; https://seelio.com/w/fgf/omnilif-the-new-standard-in-spinal-deformity-correction-and-fusion?student=lumbarjax; dated Nov. 27, 2014, 11 pages.
Application and File History for U.S. Appl. No. 12/407,608, filed Mar. 19, 2009, now U.S. Pat. No. 8,628,577, Inventors Jimenez et al.
Application and File History for U.S. Appl. No. 12/650,994, filed Dec. 31, 2009, now U.S. Pat. No. 8,523,944, Inventors Jimenez et al.
Application and File History for U.S. Appl. No. 12/651,266, filed Dec. 31, 2009, now U.S. Pat. No. 8,540,452, Inventors Jimenez et al.
Application and File History for U.S. Appl. No. 12/841,465, filed Jul. 22, 2010, now U.S. Pat. No. 8,303,663, Inventors Jimenez et al.
Application and File History for U.S. Appl. No. 12/841,869, filed Jul. 22, 2010, Now U.S. Pat. No. 9,358,125, Inventors Jimenez et al.
Application and File History for U.S. Appl. No. 13/189,410, filed Jul. 22, 2011, now U.S. Pat. No. 8,636,746, Inventor Jimenez.
Application and File History for U.S. Appl. No. 13/661,534, filed Oct. 26, 2012, now U.S. Pat. No. 8,932,302, Inventor Jimenez.
Application and File History for U.S. Appl. No. 13/591,463, filed Aug. 22, 2012, now U.S. Pat. No. 8,771,360, Inventor Jimenez.
Application and File History for U.S. Appl. No. 13/891,356, filed May 10, 2013, now U.S. Pat. No. 8,906,100, Inventor Jimenez et al.
Application and File History for U.S. Appl. No. 14/024,764, filed Sep. 12, 2013, now U.S. Pat. No. 9,381,092, Inventor Jimenez et al.
Application and File History for U.S. Appl. No. 14/153,281, filed Jan. 13, 2014, now U.S. Pat. No. 9,867,717, Inventor Jimenez.
Application and File History for U.S. Appl. No. 14/563,660, filed Dec. 8, 2014, now U.S. Pat. No. 9,445,917, Inventor Jimenez et al.
Application and File History for U.S. Appl. No. 14/242,451, filed Apr. 1, 2014, now U.S. Pat. No. 8,940,049, Inventor Jimenez et al.
Application and File History for U.S. Appl. No. 14/318,196, filed Jun. 27, 2014, now U.S. Pat. No. 9,474,626, Inventor Jimenez et al.
Application and File History for U.S. Appl. No. 14/592,507, filed Jan. 8, 2015, now U.S. Pat. No. 9,498,270, Inventor Jimenez et al.
Application and File History for U.S. Appl. No. 14/585,544, filed Dec. 30, 2014, now U.S. Pat. No. 9,486,328, Inventor Jimenez et al.
Application and File history for U.S. Appl. No. 15/164,498, filed May 25, 2016, now U.S. Pat. No. 9,668,879, Inventors: Jimenez et al.
Application and File history for U.S. Appl. No. 15/174,454, filed Jun. 6, 2016, now U.S. Pat. No. 10,117,757. Inventors: Jimenez et al.
Application and File history for U.S. Appl. No. 15/332,066, filed Oct. 24, 2016, now U.S. Pat. No. 10,369,008. Inventors: Jimenez et al.
Application and File history for U.S. Appl. No. 15/591,214, filed May 10, 2017, now U.S. Pat. No. 10,052,214. Inventors: Jimenez et al.
Application and File history for U.S. Appl. No. 15/198,557, filed Jun. 30, 2016, now U.S. Pat. No. 10,060,469, Inventors: Jimenez et al.
Application and File history for U.S. Appl. No. 16/184,509, filed Nov. 8, 2018. Inventors: Jimenez et al.
Application and File history for U.S. Appl. No. 16/750,784, filed Jan. 23, 2020. Inventors: Jimenez et al.
Application and File history for U.S. Appl. No. 16/292,565, filed Mar. 5, 2019. Inventors: Jimenez et al.
International Search Report and Written Opinion for International Application No. PCT/US2019/068890 dated Apr. 29, 2020.

* cited by examiner

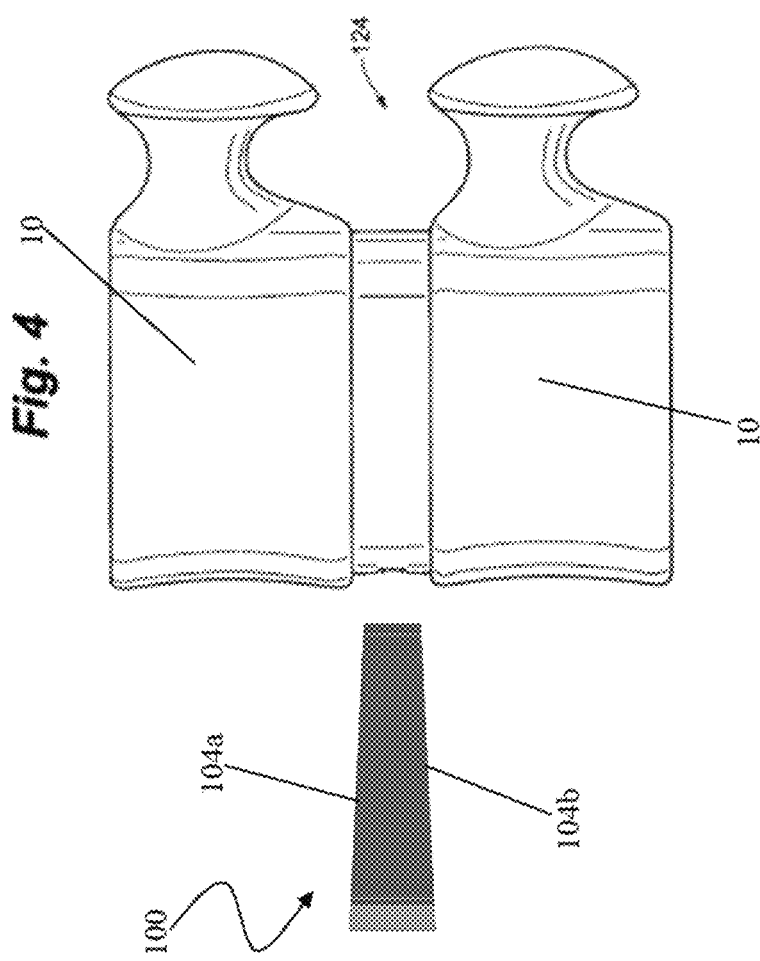

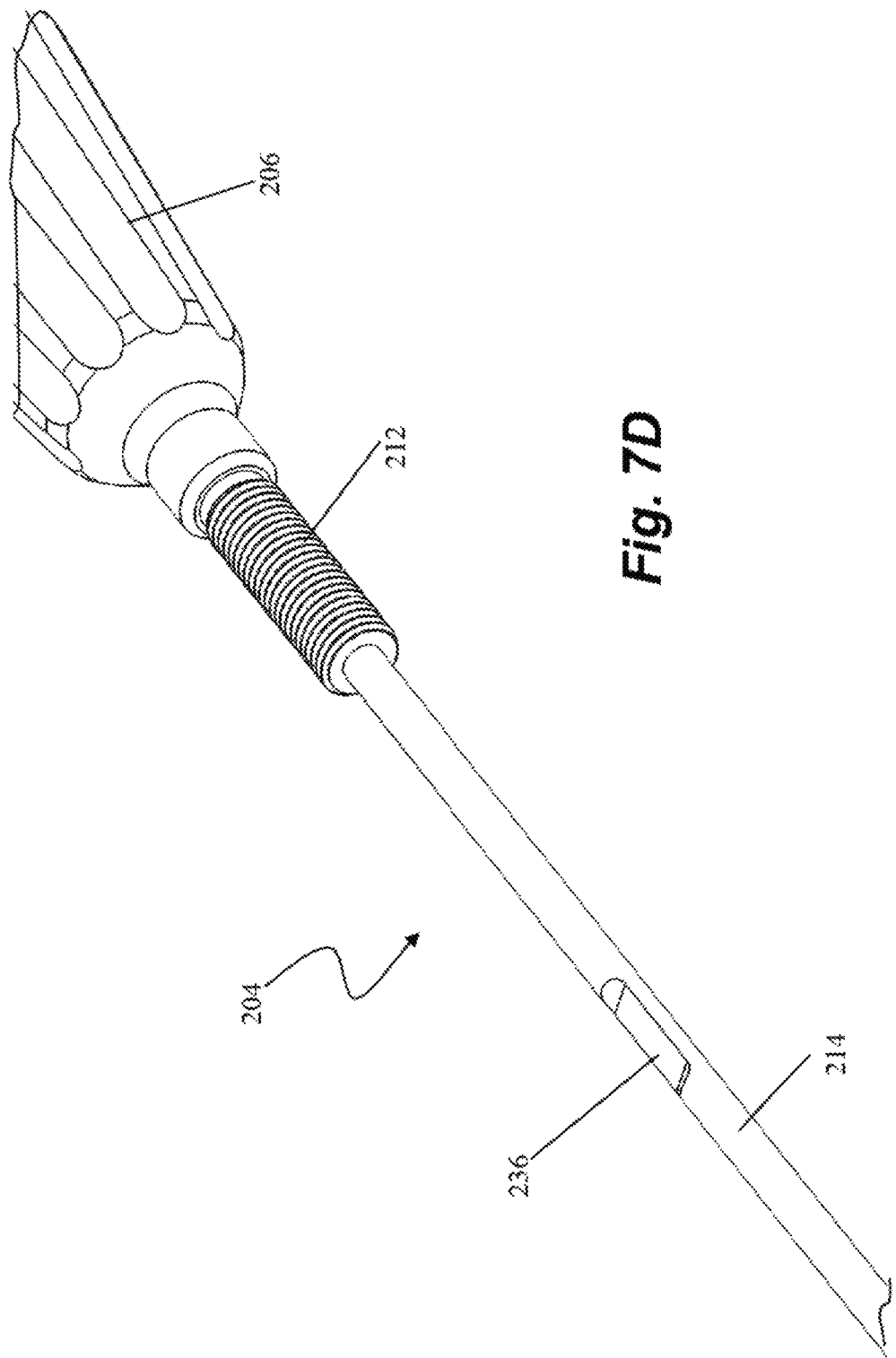

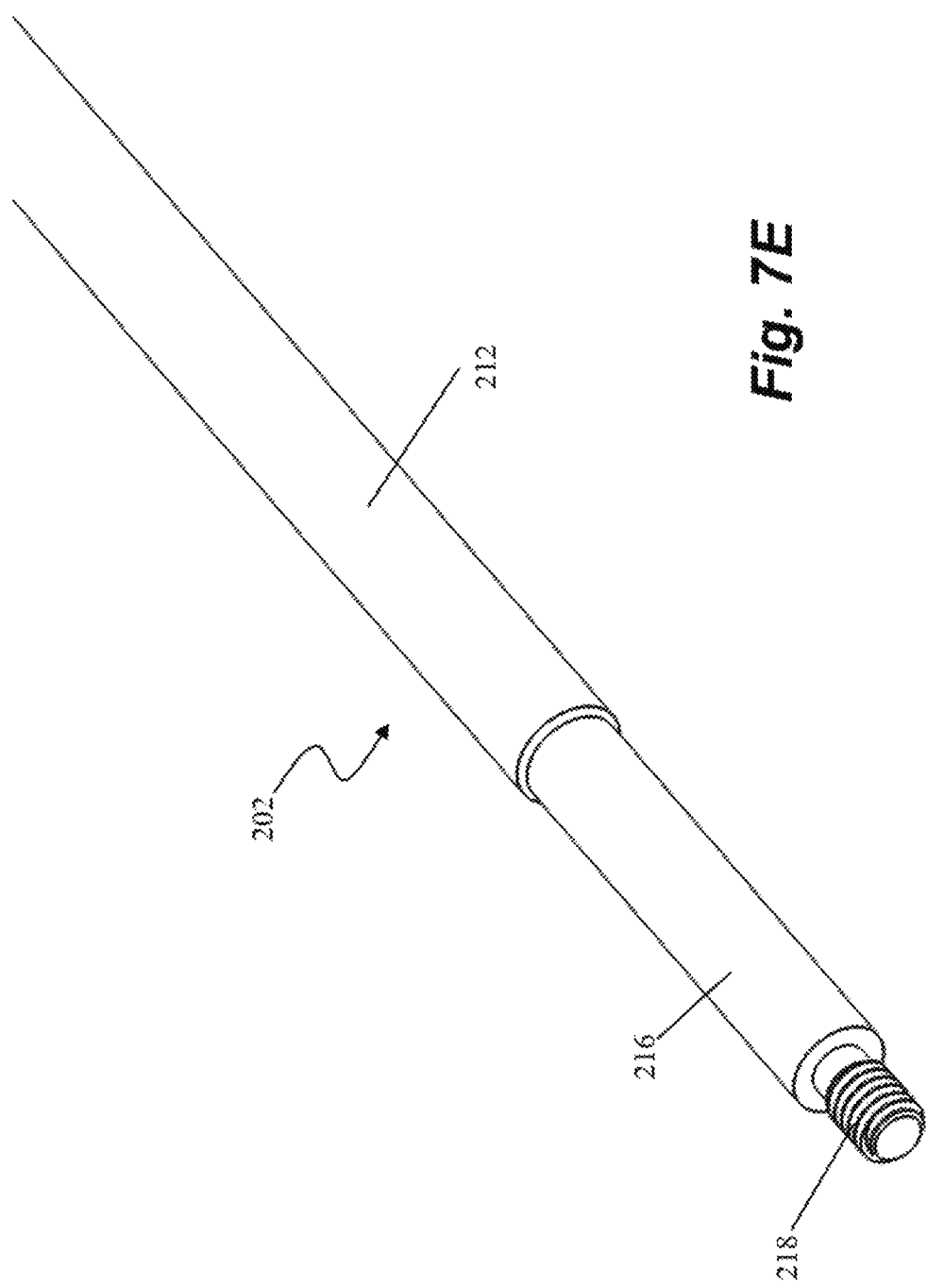

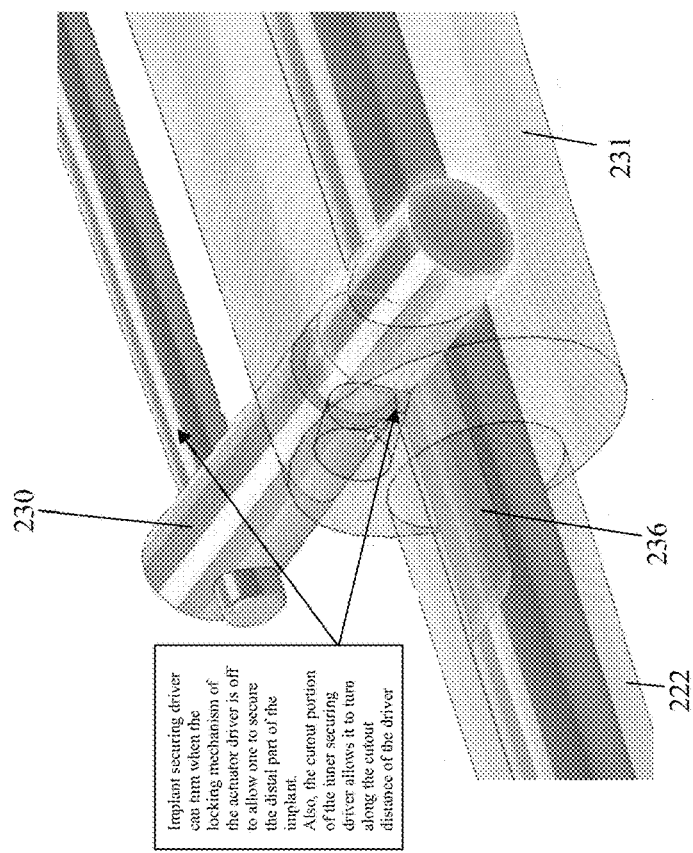
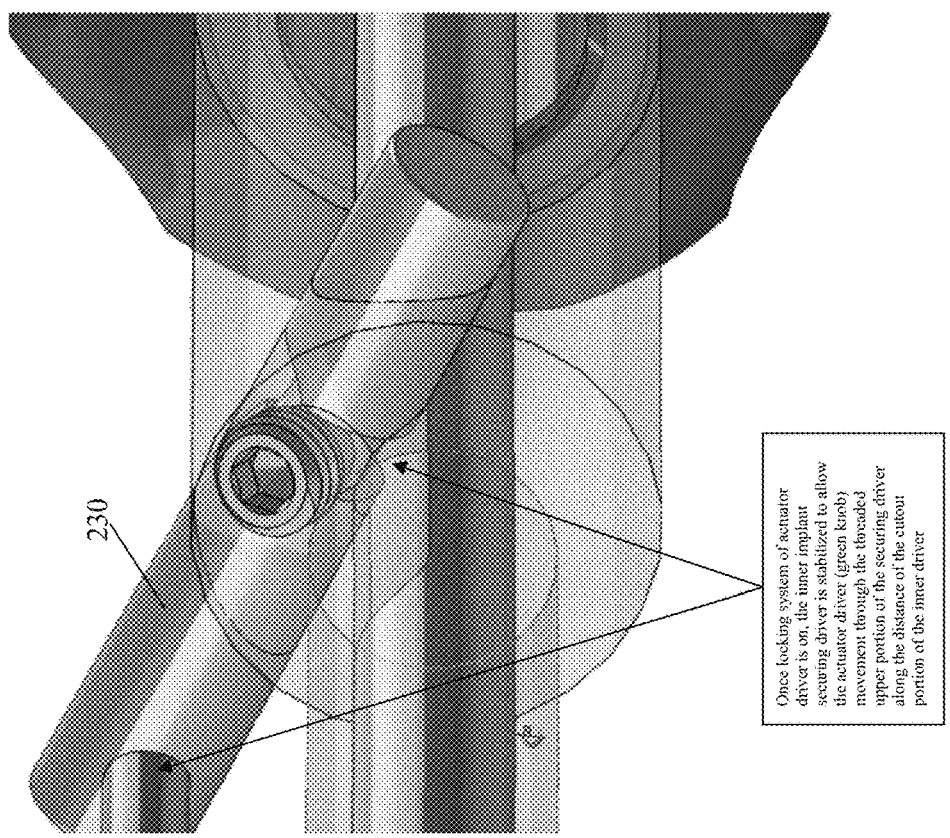
Fig. 9E
Fig. 9F

TRANSVERSELY EXPANDABLE MINIMALLY INVASIVE INTERVERTEBRAL CAGE AND INSERTION AND EXTRACTION DEVICE

RELATED APPLICATION

The present application is a Continuation-in-Part of U.S. patent application Ser. No. 16/292,565, filed Mar. 5, 2019, which is incorporated by reference herein in its entirety.

TECHNICAL FIELD

The present invention relates to the fusion of vertebral bodies. More specifically, the present invention relates to devices and associated methods for fusion of vertebral bodies that provide robust spinal support in a less invasive manner.

BACKGROUND

The concept of intervertebral fusion for the cervical and lumbar spine following a discectomy was generally introduced in the 1960s. It involved coring out a bone graft from the hip and implanting the graft into the disc space. The disc space was prepared by coring out the space to match the implant. The advantages of this concept were that it provided a large surface area of bone to bone contact and placed the graft under loading forces that allowed osteoconduction and induction enhancing bone fusion. However, the technique is seldom practiced today due to numerous disadvantages including lengthy operation time, destruction of a large portion of the disc space, high risk of nerve injury, and hip pain after harvesting the bone graft.

Presently, at least two devices are commonly used to perform the intervertebral portion of an intervertebral body fusion: the first is the distraction device and the second is the intervertebral body fusion device, often referred to as a cage. Cages can be implanted as standalone devices or as part of a circumferential fusion approach with pedicle screws and rods. The concept is to introduce a distraction device that will distract a collapsed disc in a generally axial direction, decompress the nerve root, and allow load sharing to enhance bone formation, and then implant an intervertebral fusion device that is small enough to allow implantation with minimal retraction and pulling on nerves.

In a typical intervertebral body fusion procedure, a portion of the intervertebral disc is first removed from between the vertebral bodies. This can be done through either a direct open approach or a minimally invasive approach. Disc shavers, pituitary rongeours, curettes, and/or disc scrapers can be used to remove the nucleus and a portion of either the anterior or posterior annulus to allow implantation and access to the inner disc space. The distraction device is inserted into the cleared space to enlarge the disc space such that the vertebral bodies are separated in a generally axial direction by actuating the distraction device. Enlarging the disc space is important because it also opens the foramen where the nerve root exists. It is important that during the distraction process one does not over-distract the facet joints. An intervertebral fusion device is next inserted into the distracted space and bone growth factor, such as autograft, a collagen sponge with bone morphogenetic protein, or other bone enhancing substance may be inserted into the space within the intervertebral fusion device to promote the fusion of the vertebral bodies.

Intervertebral distraction and fusion can be performed through anterior, posterior, oblique, and lateral approaches. Each approach has its own anatomical challenges, but the general concept is to fuse adjacent vertebra in the cervical thoracic or lumbar spine. Devices have been made from various materials. Such materials include cadaveric cancellous bone, carbon fiber, titanium and polyetheretherketone (PEEK). Devices have also been made into different shapes such as a bean shape, football shape, banana shape, wedge shape and a threaded cylindrical cage.

As with all minimally invasive surgeries, a primary goal is to provide equivalent or near equivalent treatment as more invasive surgical techniques but with less discomfort, recovery time, etc. for the patient. One problem with minimally invasive intervertebral fusion procedures is that the limited size of the surgical access limits the size of the implant(s) that can be inserted. While devices that are vertically expandable in a generally axial direction have addressed some of these issues by being able to be inserted through a smaller opening and then made taller in a generally axial direction within the disc space, such devices are still limited in the transverse footprint that can be covered within the disc space which can affect the stability of the device within the disc space and limits the area for bone grown.

SUMMARY

Disclosed herein are systems and methods for intervertebral body fusion that provide more robust support within the disc space. Intervertebral body fusion devices can have a unitary monolithic body including a plurality of body segments interconnected with each other by flexure members. Devices can be configured to be inserted through an opening in a compressed configuration and then expanded within the disc space to an expanded configuration. In the expanded configuration, devices can have a greater mediolateral or transverse to the disc space footprint. This wider footprint provides greater support for the vertebrae relative to the size of the opening through which the device is inserted. Insertion devices for inserting, expanding and extracting such implants are also disclosed.

In one embodiment, an expandable intervertebral body fusion device includes a unitary monolithic body having a plurality of body segments connected to each other with flexure members and an opening defined between the plurality of body segments. The device body can include an anterior body segment, a posterior body segment and one or more mediolateral body segments extending between the anterior body segment and the posterior body segment along both a lateral side and a medial side of the anterior body segment and the posterior body segment. A threaded opening can be formed in one or more of the anterior body segment and the posterior body segment. The body is configured to be mediolaterally expanded from a compressed configuration to an expanded configuration by interaction of an expansion tool with the threaded opening causing the one or more mediolateral body segments on the lateral side and the one or more mediolateral body segments on the medial side to generally move away from each other and expand the opening between the plurality of body segments such that the body forms a greater mediolateral footprint in the expanded configuration than in the compressed configuration.

In one embodiment, a transversely expandable intervertebral body fusion device for a disc space between adjacent vertebrae of a spine of a human patient includes a unitary monolithic body configured in size and shape to be implantable in the disc space. The body can have at least four body segments each connected to adjacent body segments by one or more flexure members with the body segments surrounding and collectively defining an opening within a transverse plane bisecting the body. The body segments can include an anterior body segment, a posterior body segment and at least one mediolateral body segment extending between the anterior body segment and the posterior body segment along each of a lateral side and a medial side of the body. A threaded opening can be formed in at least one of the anterior body segment and the posterior body segment. The body can be configured to be mediolaterally expanded from a transversely compressed configuration to a transversely expanded configuration by interaction of an expansion tool with the threaded opening causing the at least one mediolateral body segments on each side to generally move transversely away from each other, thereby expanding the opening of the body and forming a perimeter defined by an outer edge of the body that presents a mediolateral footprint in the expanded configuration that is greater than in the compressed configuration.

In an embodiment, an insertion device is provided for inserting and expanding an expandable intervertebral body fusion device in an intervertebral disc space defined between adjacent vertebrae of a patient. Insertion device can include a stabilizing shaft having a stabilizing tip with a stabilizing handle configured to rotate the stabilizing shaft to engage the stabilizing tip with a distal portion of the expandable intervertebral body fusion device. Insertion device can further include an expansion shaft having an expansion tip with the expansion shaft having an internal lumen enabling passage of the stabilizing shaft and the stabilizing tip through the expansion shaft and distally beyond the expansion tip. An expansion shaft handle can be configured to rotate the expansion shaft to engage the expansion tip with a proximal portion of the expandable intervertebral body fusion device. A shaft lock can be configured to selectively lock the stabilizing shaft to prevent rotation of the stabilizing shaft while enabling rotation of the expansion shaft. Device can further include an actuation handle configured to rotate the expansion shaft when the shaft lock has locked the stabilizing shaft causes the expansion shaft to advanced the expansion shaft in an axial direction relative to the stabilizing shaft to press the proximal portion of the expandable intervertebral body fusion device towards the distal portion of the expandable intervertebral body fusion device to cause the expandable intervertebral body fusion device to expand in a direction transverse to the axial direction.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIG. 4 depicts a schematic representation of an expandable intervertebral body fusion device according to an embodiment being inserted between vertebrae of a patient.

FIGS. 7A-7F depict portions of an insertion device for an expandable intervertebral body fusion device according to an embodiment.

FIGS. 9A-9I depict portions of an insertion device and an expandable intervertebral body fusion device according to an embodiment FIG. 10D is a cross-sectional view taken along the line A-A in FIG. 10C, FIG. 10E is a cross-sectional view taken along the line B-B in FIG. 10D, and FIGS. 10F and 10G are cross-sectional views taken along the lines C-C and D-D in FIG. 10E, respectively.

Figure 1A:
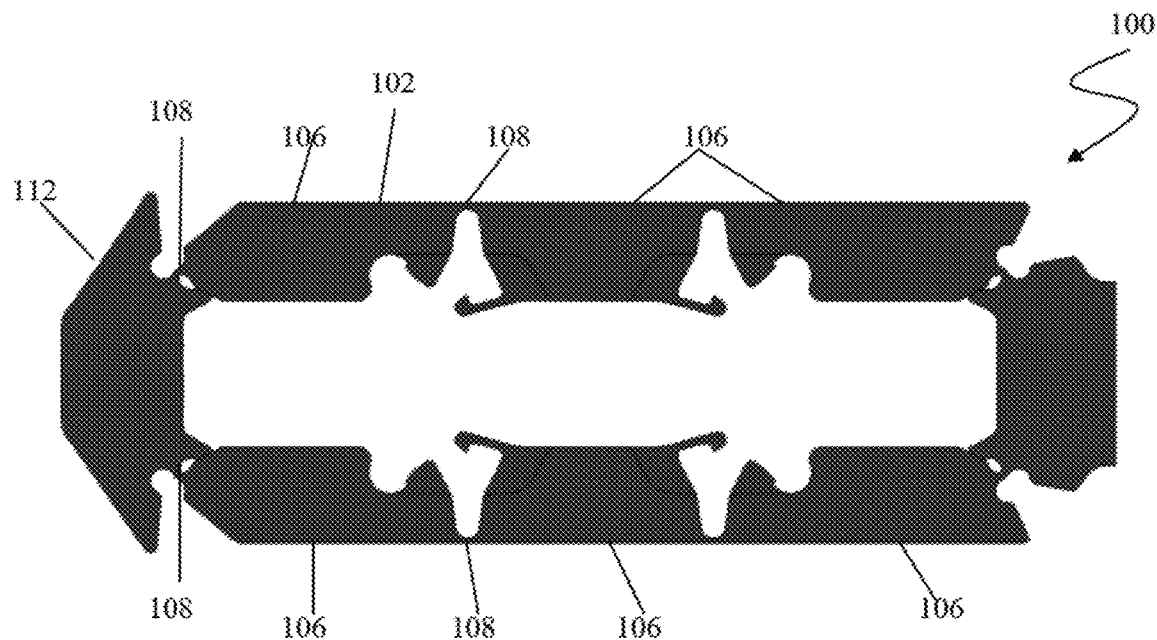
FIGS. 1A-1D depict an expandable intervertebral body fusion device in a collapsed configuration according to an embodiment.
Figure 1B:
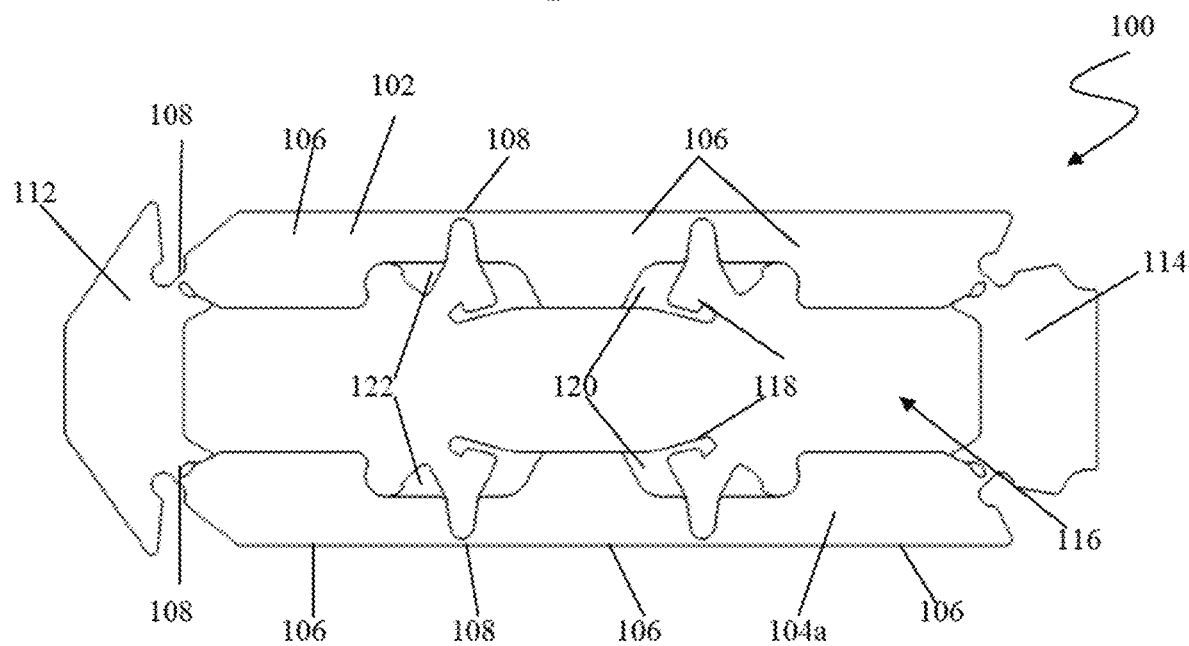
Figure 1C:
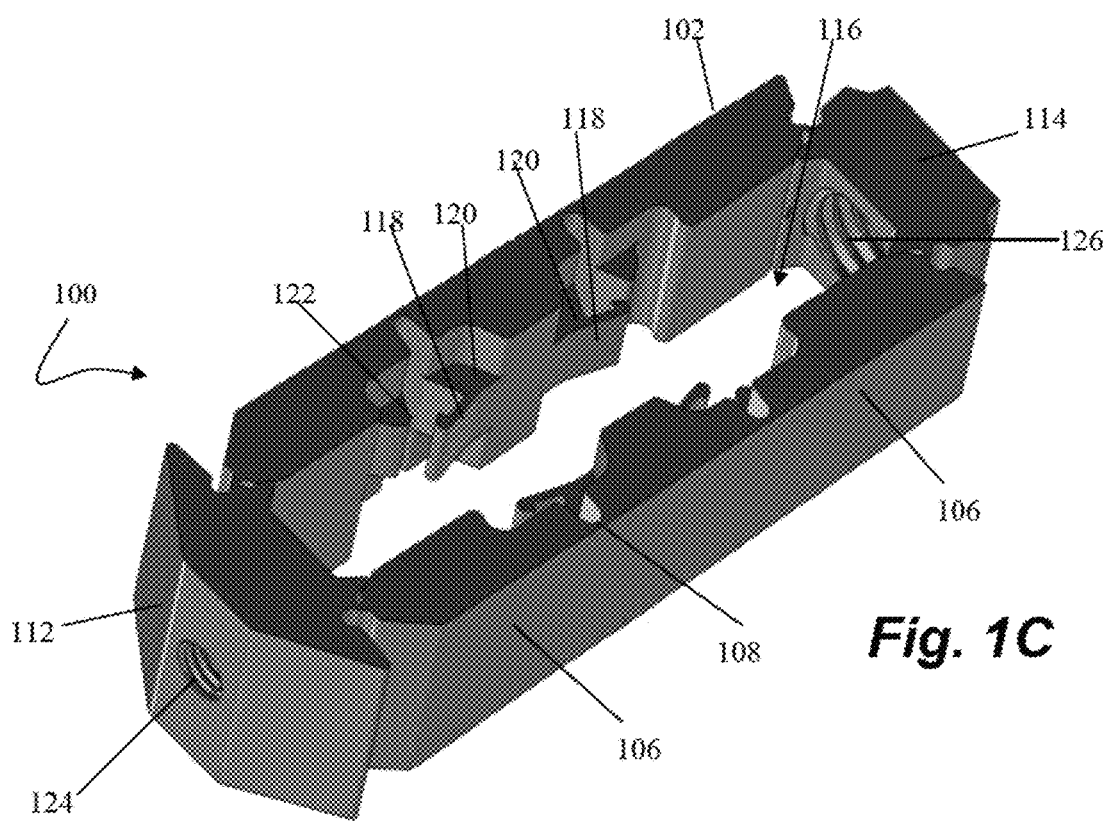
Figure 1D:
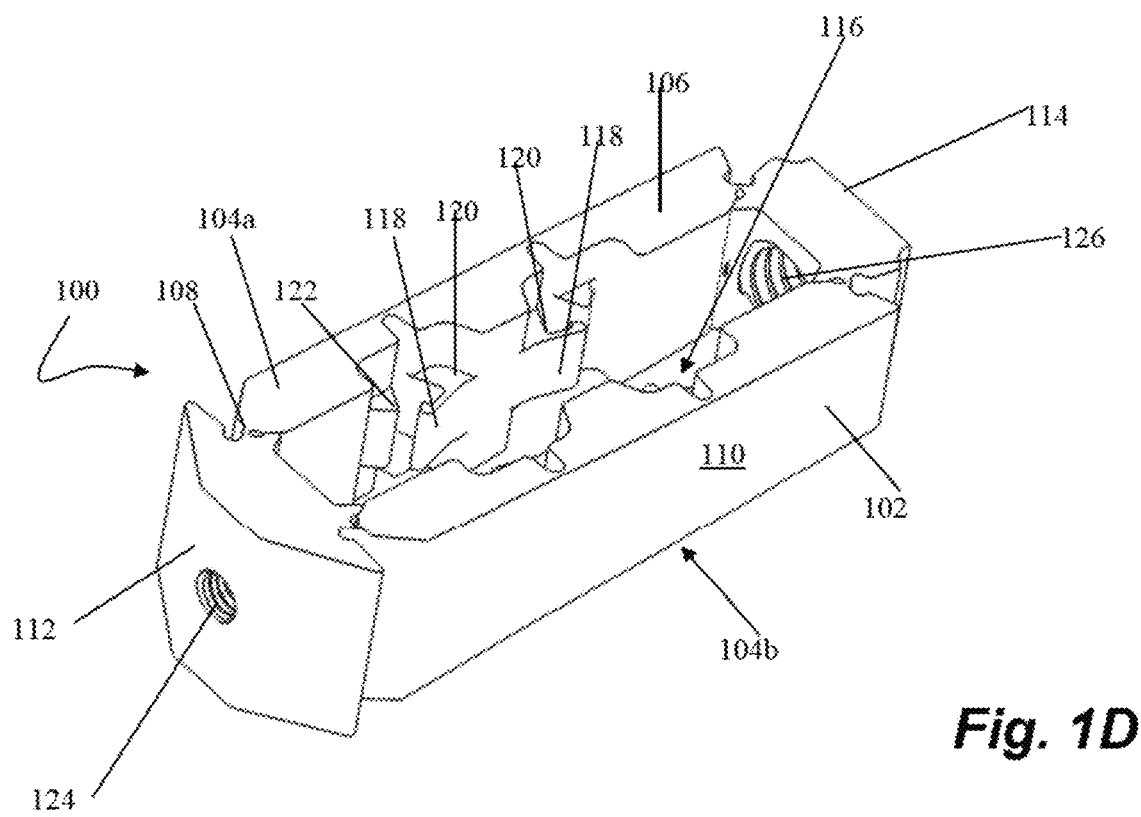
Figure 2B:
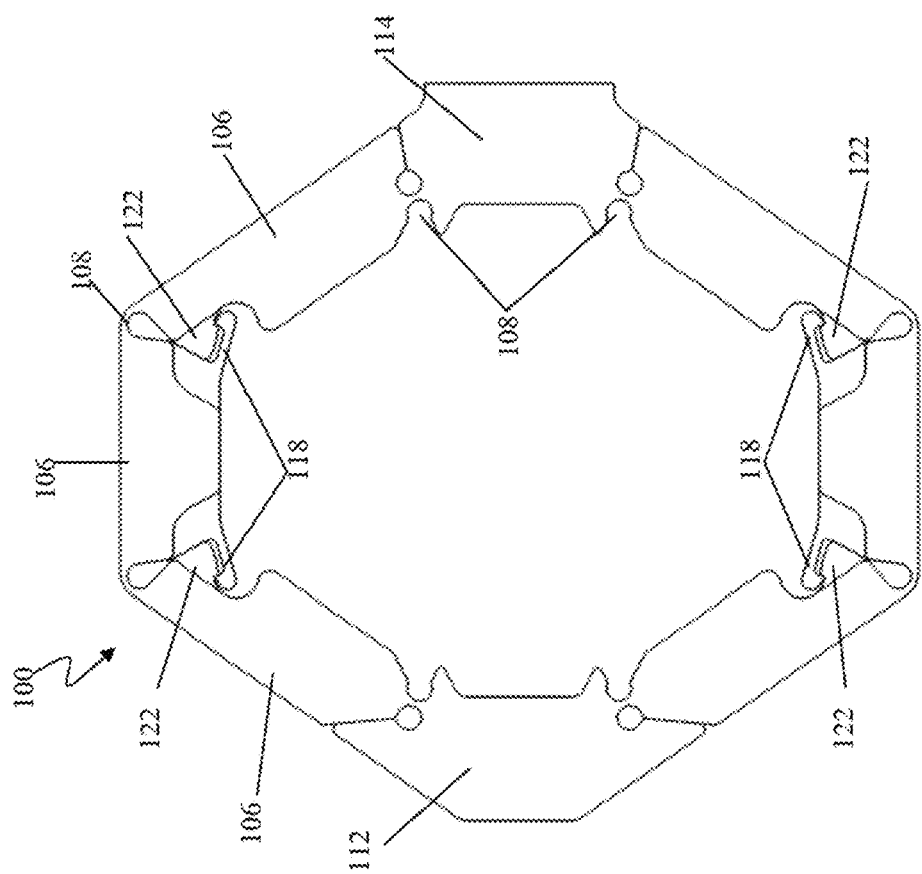
FIGS. 2A-2D depict the expandable intervertebral body fusion device of FIGS. 1A-1D in an expanded configuration.
Figure 2A:
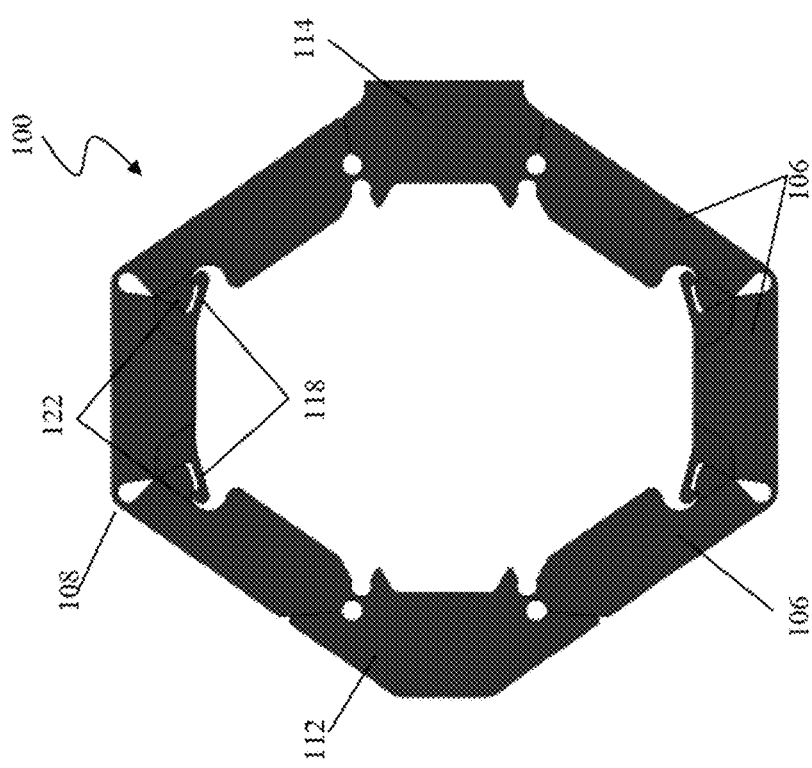
Figure 2D:
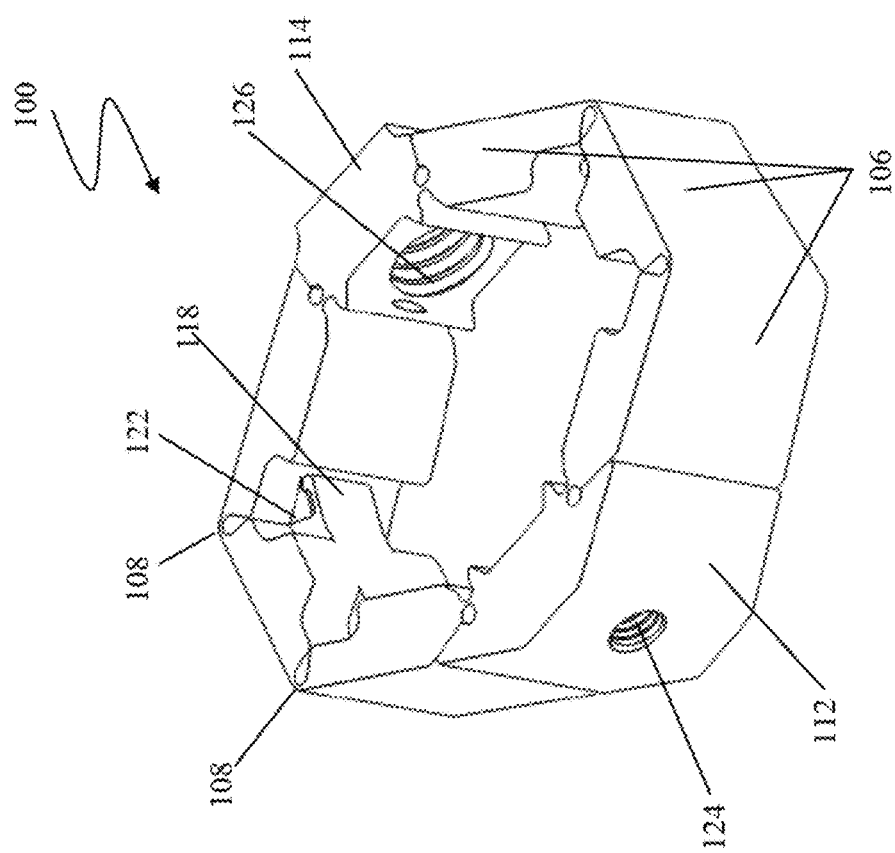
Figure 2C:
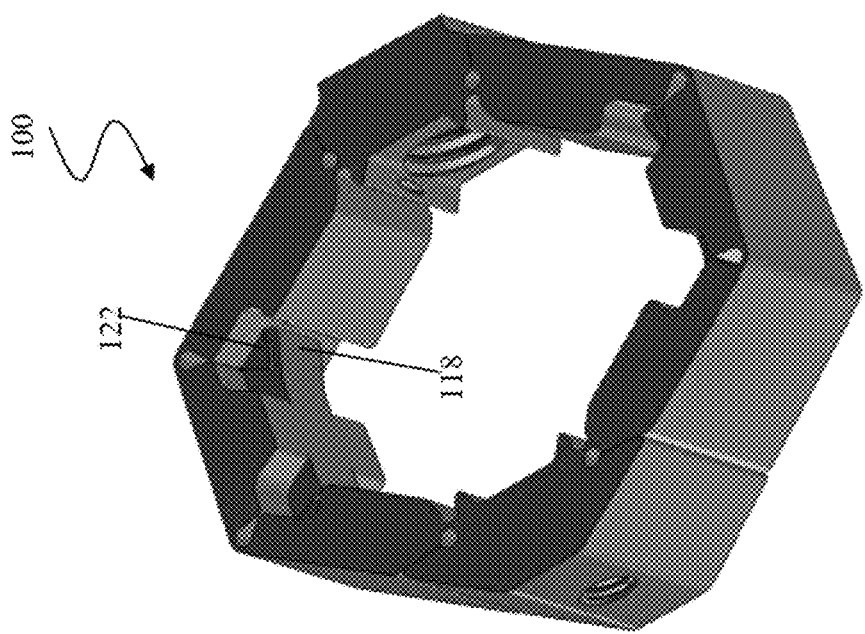

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

FIGS. 1A-1D and 2A-2D depict an expandable intervertebral body fusion device 100 according to an embodiment. FIGS. 1A-1D depict the device 100 in a collapsed configuration and FIGS. 2A-2D depict the device 100 in an expanded configuration. In practice, the device 100 is inserted into the disc space through a minimally invasive access in the collapsed configuration and then expanded inside of the disc space. In embodiments, the device 100 is inserted between adjacent vertebrae 10 on its side as depicted in FIG. 4 such that when it is expanded in the disc space rather than expanding vertically it expands horizontally/transversely to the disc space to enable the device to take up a larger footprint within the disc space as can be seen contrasting FIG. 5A and FIG. 5B. The device is therefore able to occupy more lateral to medial and anterior to posterior space within the disc space relative to the size of the access that has heretofore been possible. In one embodiment in its insertion and un-expanded state the device is 8 mm in height, 11.5 mm in width and 26 mm in length. The device can have many heights from 8 mm up to 16 mm. In embodiments, the width can go from 8-12 mm and the length from 22 mm-32 mm. When the device is expanded, the height remains the same but the width can double or nearly double (from 11.5 to 22 mm or 47%) and the length goes from 26 mm to 20 mm (16% decrease). The device can have many lordotic angles from 0 to 15 degrees or higher; the most common being 0, 6, 12 degrees. The horizontal top and bottom of the device can have different shapes to better fit the endplates such as football shaped or domed. Also, the different segments of the device separated by flexures could be tailored or cut by wire EDM or 3D printed to create different horizontal expanded states such as oval, elliptical, circular, bean shaped, banana shaped or many other polygons and non-polygon shapes. The mean disc height at the L3-4 level is 11.3 mm+/−1.8 mm, L4-5 11.3+/−2.1 mm and L5-S1 10.7+/−2.1 mm. The average circumference of the L4 endplate is about 141 mm and surface area 1,492 mm² above. The device can have difference foot prints to try to fill the endplate or disc space circumference.

Referring now to FIGS. 1A-1D, device 100 can include a device body 102. Generally, device body 102 can be unitarily formed as a single monolithic construct, although multiple component embodiments are also contemplated. Device body 102 can include upper 104a and lower 104b bearing surfaces. As noted above, device 100 can be inserted generally on its side such that bearing surfaces 104a, 104b interface with and bear the forces of the adjacent vertebrae 10 (see FIGS. 4 and 5A-5B). In embodiments, the larger threaded opening 126 are positioned dorsal or posterior and the smaller opening 124 is positioned ventral or anterior. Device body 102 can include a plurality of mediolateral body segments 106 unitary connected to each other by flexure 108 comprising a thin, flexible strip of material. As can be seen in, e.g., FIGS. 1C-1D, mediolateral body segments 106 and flexures 108 can perform a continuous, unitary out perimeter surface 110. Device body 102 can further include an anterior body segment 112 and posterior body segment 114. Anterior and posterior body segments 112, 114 can also be connected with mediolateral body segments by flexures 108. Device body 102 further defines an open interior 116 between the body segments.

In the depicted embodiment, the device 100 includes three mediolateral body segments 106 on each side such that the device includes a total of eight body segments. In some embodiments, a device having eight body segments may be generally octagonally shaped in the expanded configuration as depicted in FIGS. 2A-2D. In other embodiments, device may have greater or fewer mediolateral body segments on each side.

Device body 102 can further include a plurality of locking flexures 118 disposed in the open interior 116. As can be seen in, e.g., FIGS. 1C-1D, locking flexures 118 can extend from a lock base 120 that is recessed with respect to bearing surfaces 104a, 104b. As will be described in more detail below, each locking flexure 118 corresponds with locking projection 122 extending from an adjacent body segment 106.

Each of anterior body segment 112 and posterior body segment 114 can include a threaded opening that aids in insertion and expansion of device. In one embodiment, anterior body segment 112 includes an anterior threaded opening 124 configured to interface with a stabilizing element for inserting the device 100 into the disc space. Posterior body segment 114 can include a posterior threaded opening 126 that is larger than anterior opening 124 and can be configured to interface with an expansion element that is rotated to expand device body 112, which will be described in more detail below. In other embodiments, anterior opening 124 may interface with the expansion elements while posterior opening 126 interfaces with the stabilizing element. In some embodiments, anterior body segment 112 can be tapered to facilitate insertion of the device 100 into the disc space through the minimally invasive access opening.

Figure 3A:
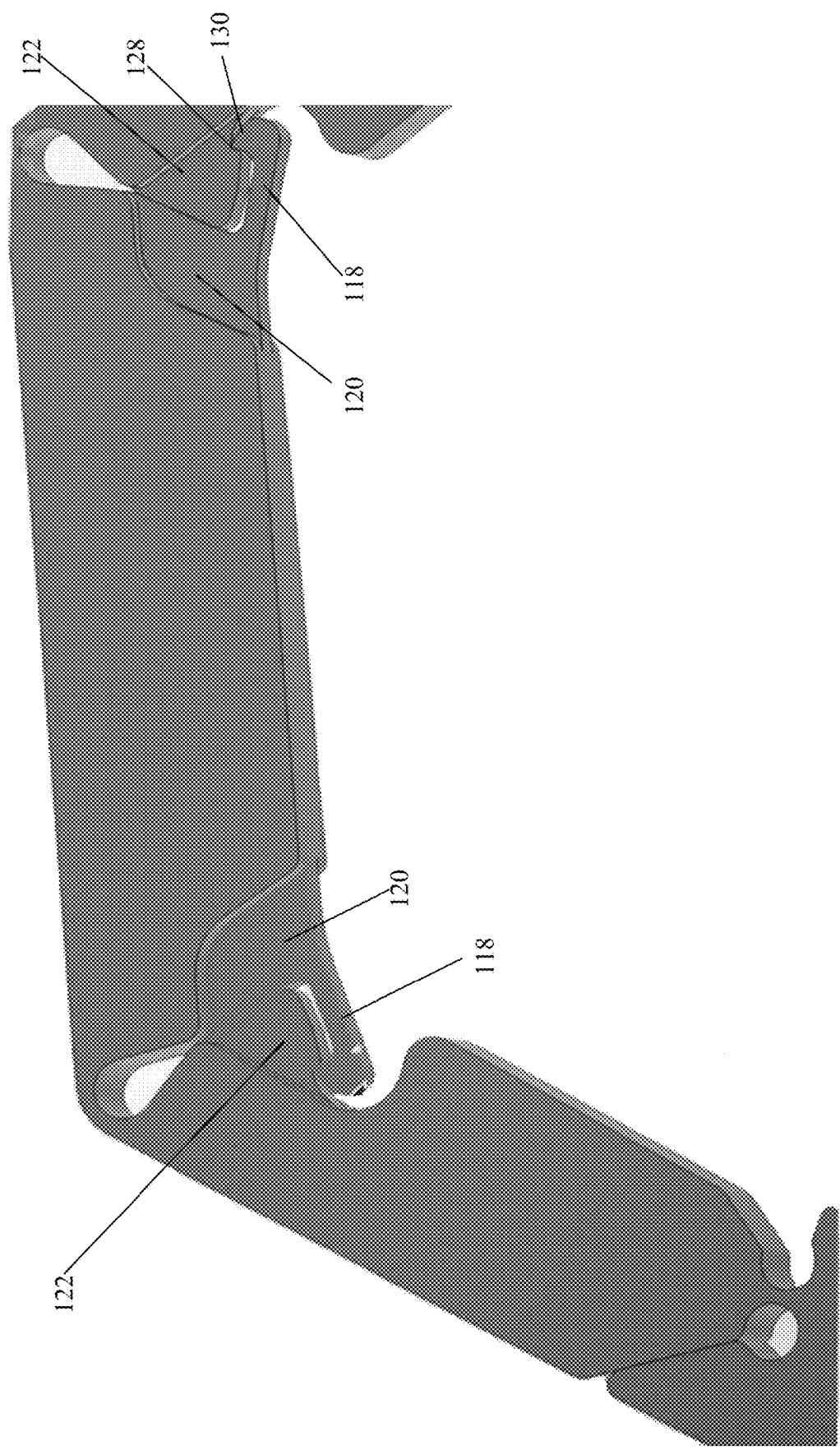
FIGS. 3A-3C depict a portion of the expandable intervertebral body fusion device of FIGS. 2A-2D.
Figure 3B:
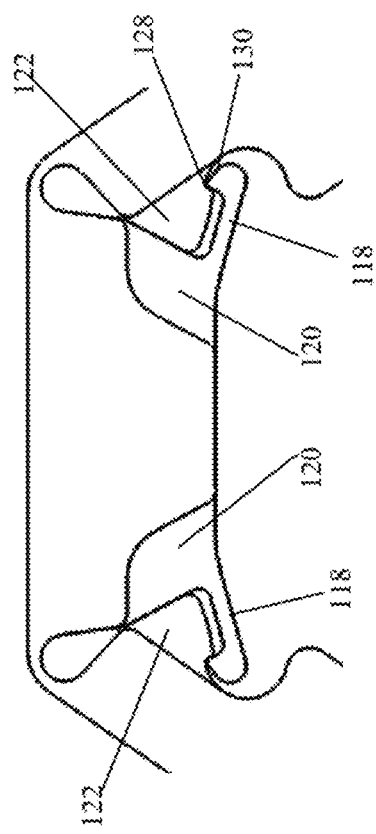
Figure 3C:
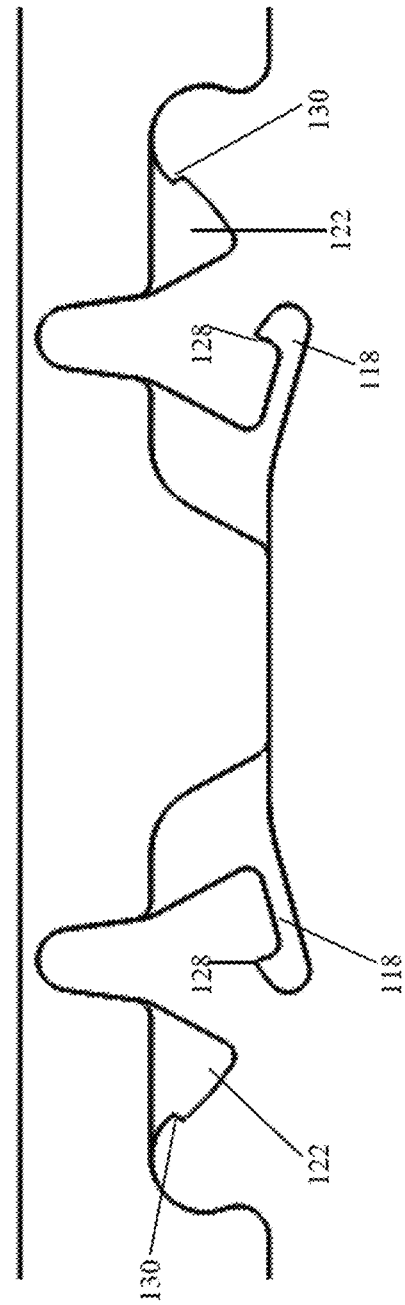

FIGS. 2A-2D depict device 100 in an expanded configuration. As the device 100 is expanded, the mediolateral body segments 106 on opposing sides of the device body 102 are moved away from each other causing the device to expand medially and laterally within the disc space. When the device 100 is expanded, the locking flexures 118 interface and lock with the locking projections 122 to prevent external forces from causes the device to compress from the expanded position following expansion. As can be seen in more detail in FIGS. 3A-3C, each locking flexure 118 includes a pointed tip 128 that interfaces with a notch 130 in locking projections to lock the components together.

Figure 5B:
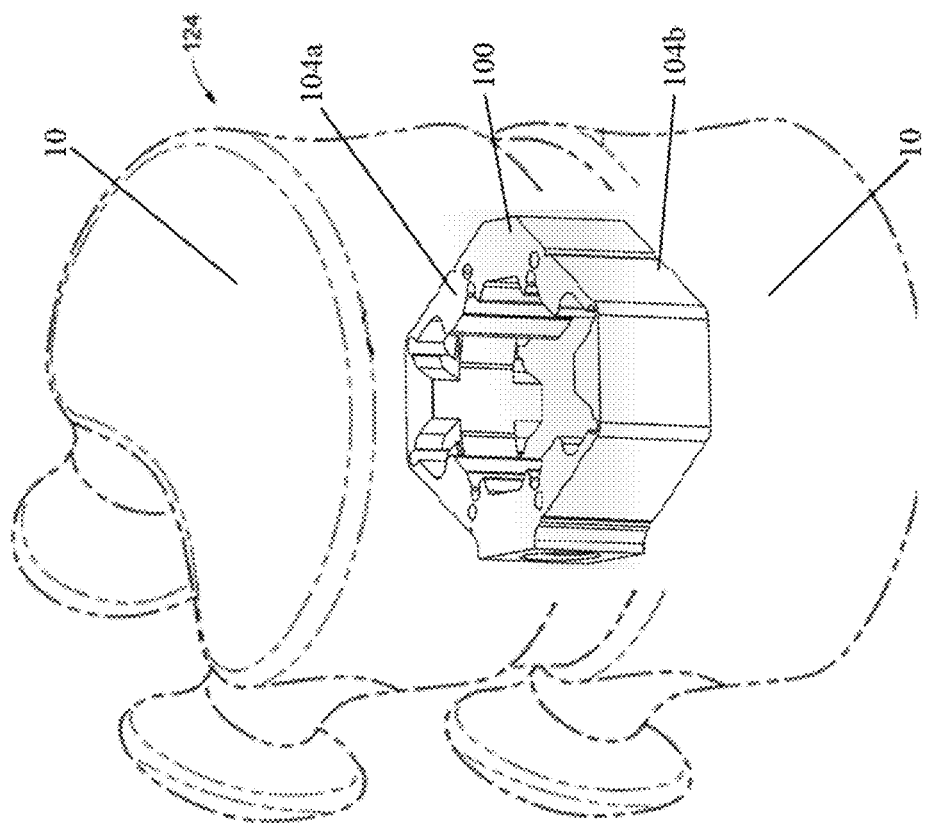
FIGS. 5A-5B depict a schematic representation of an expandable intervertebral body fusion device according to an embodiment inserted between vertebrae of a patient in a compressed and an expanded configuration.
Figure 5A:
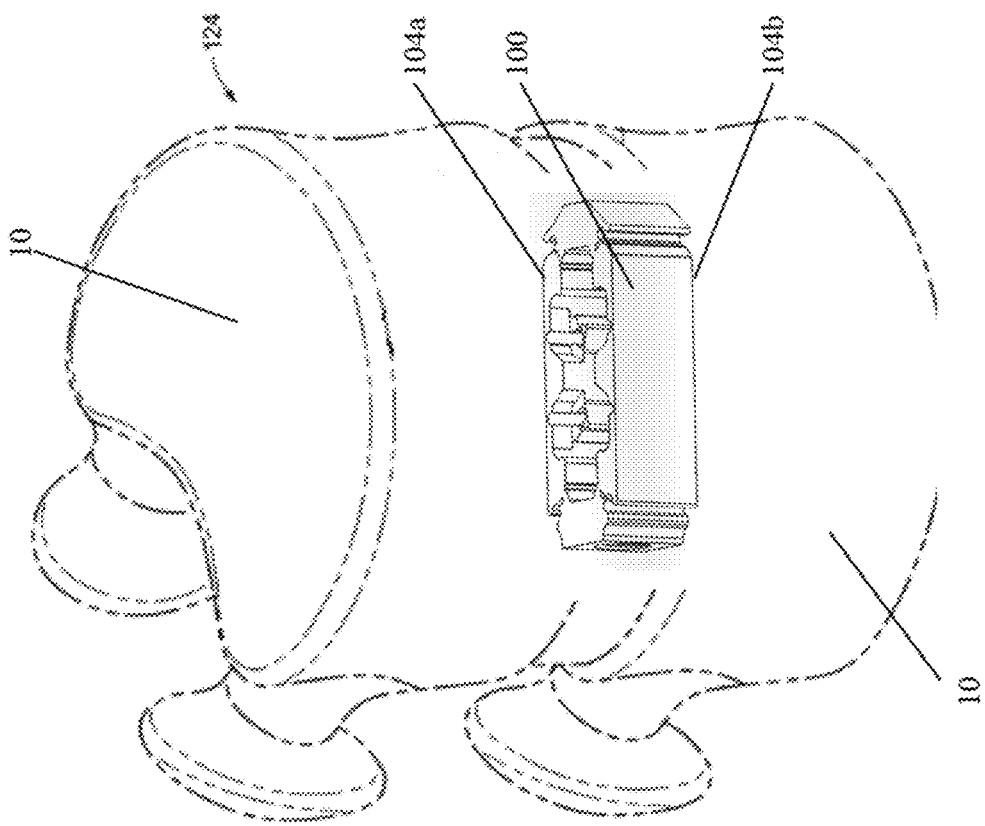

As noted above, in one embodiment device 100 is inserted between adjacent vertebrae 10 on its side, as shown in FIG. 4, with bearing surfaces 104a, 104b configured to interface with the vertebrae. FIGS. 5A-5B depict how the device 100 can be inserted in a collapsed configuration and then expanded within the disc space to occupy a greater footprint within the disc space. Note that these figures show one particular access approach and device orientation relative to the disc space, but that other access approaches and device orientations are possible.

Figure 6A:
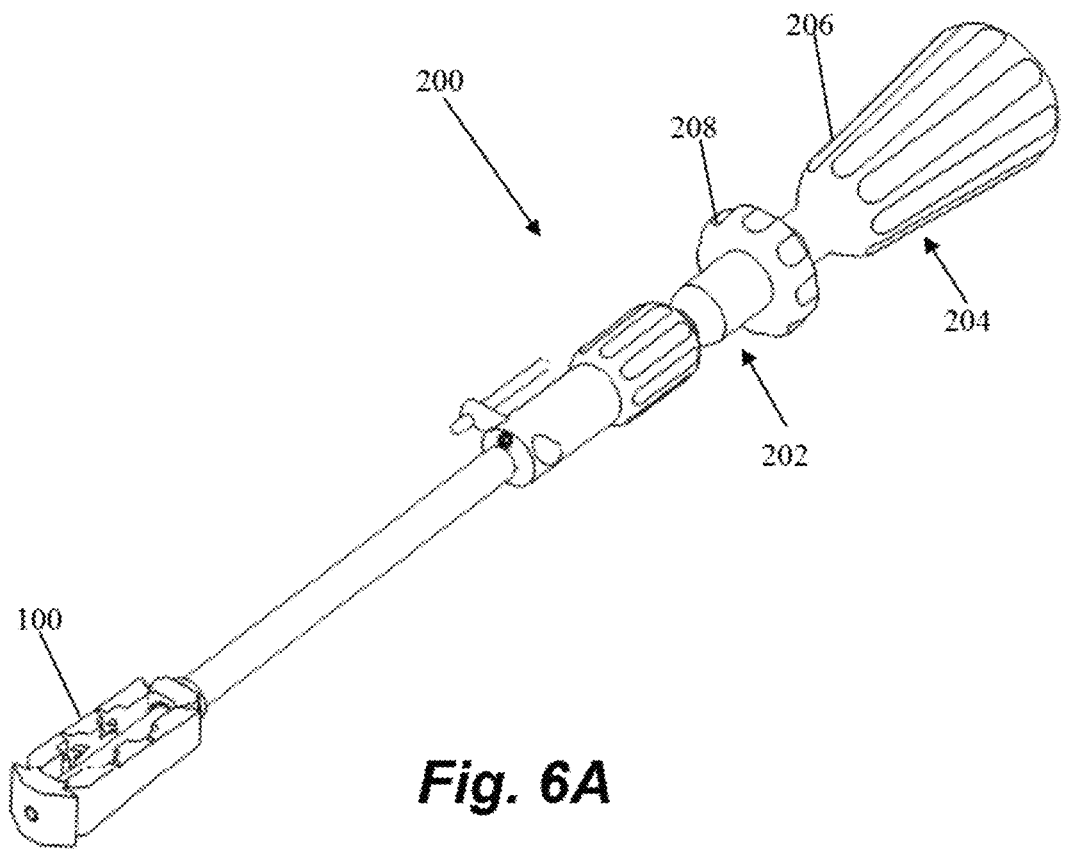
FIGS. 6A-6B depict an expandable intervertebral body fusion device and a corresponding insertion device according to an embodiment.
Figure 6B:
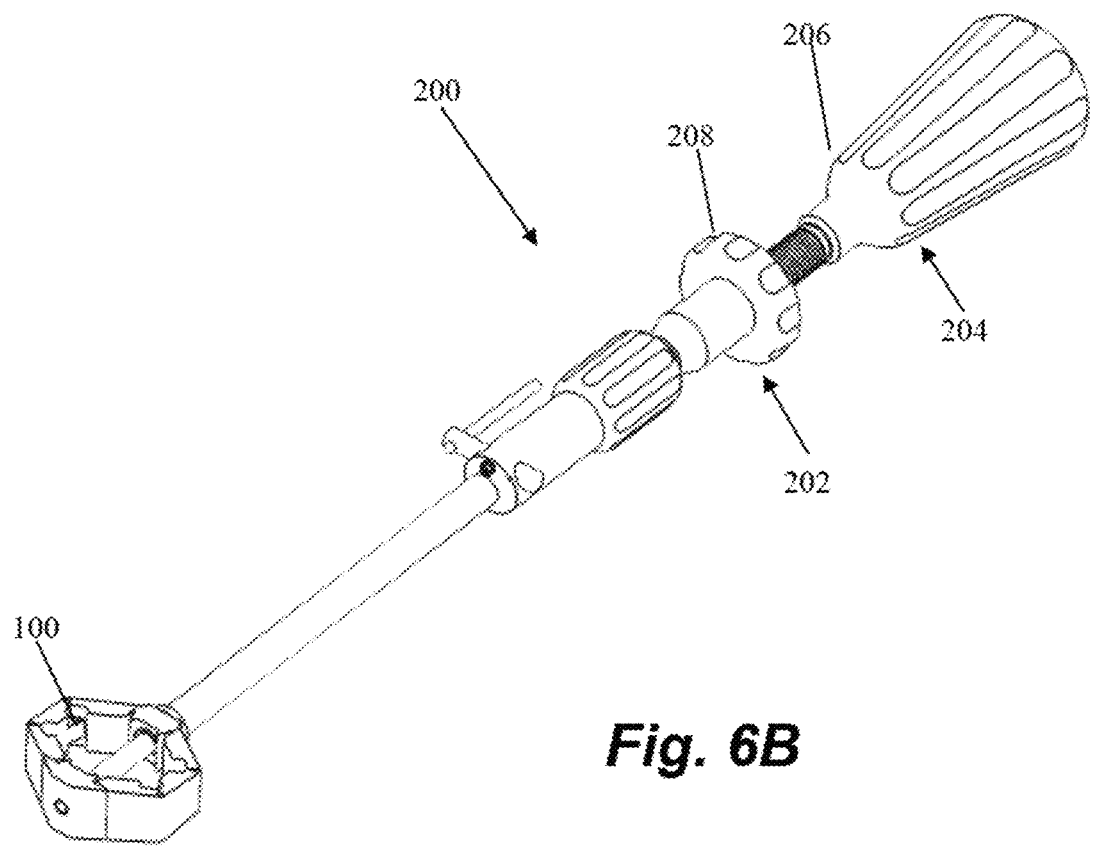
Figure 7A:
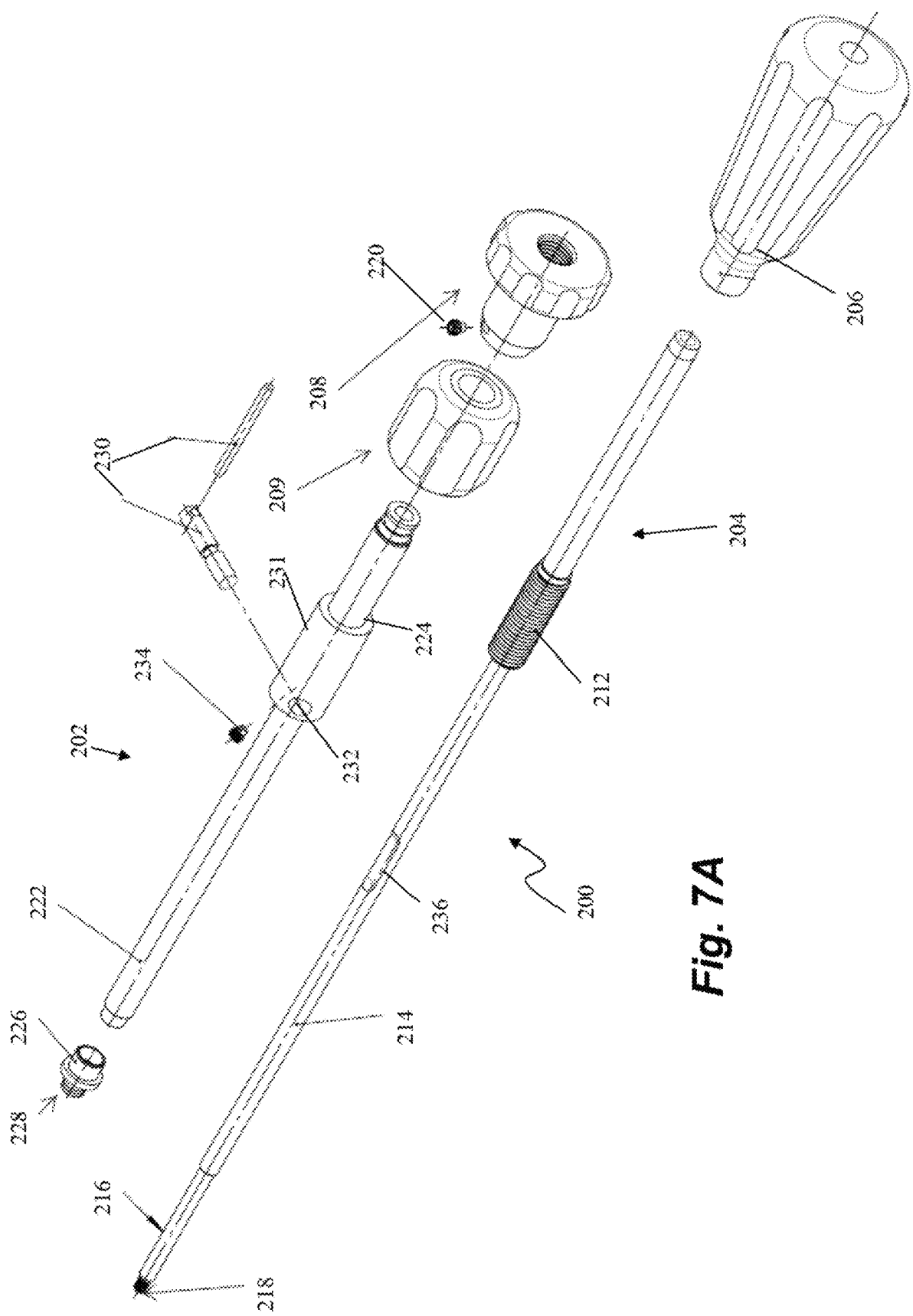
Figure 7B:
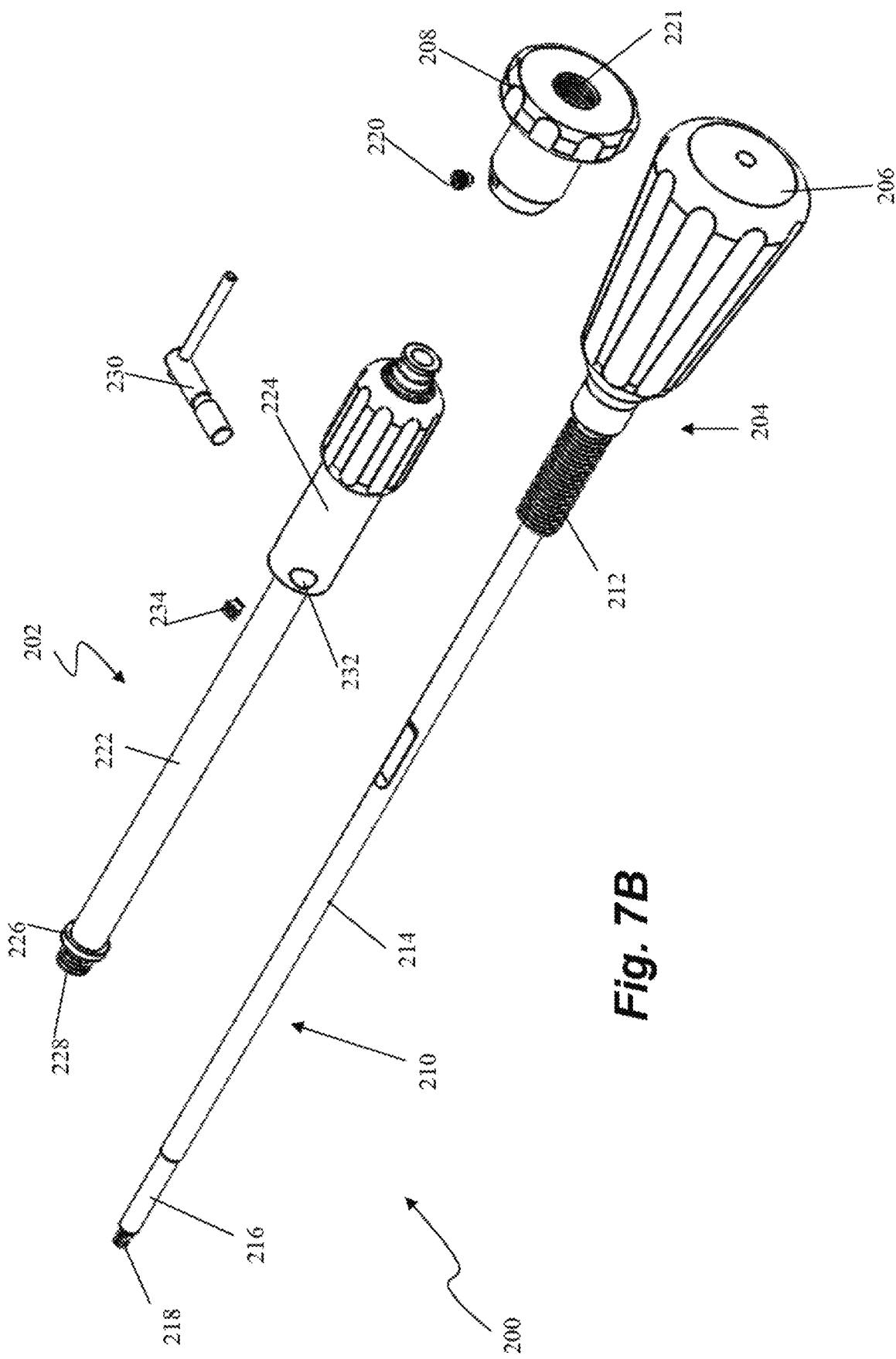
Figure 7C:
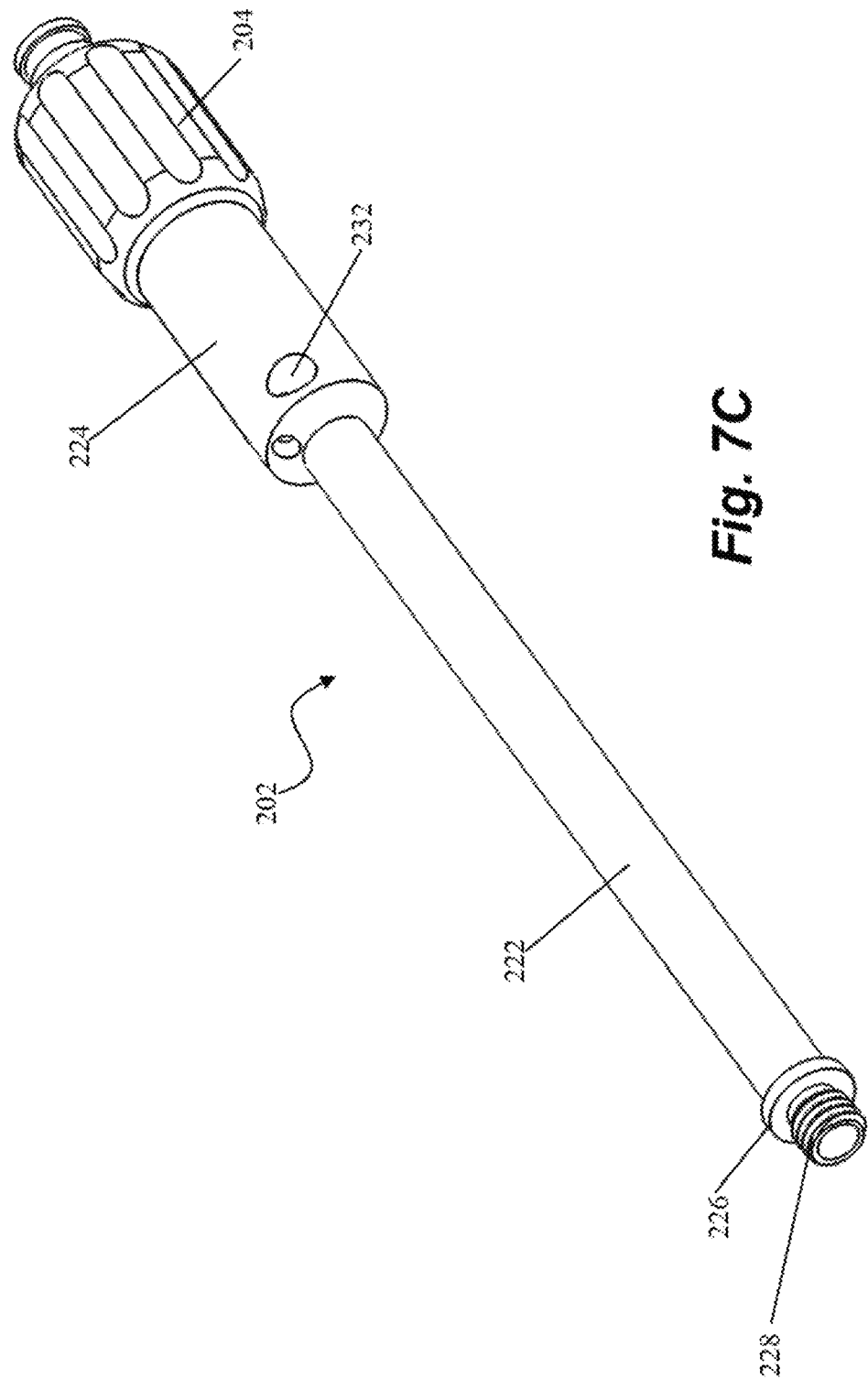
Figure 7F:
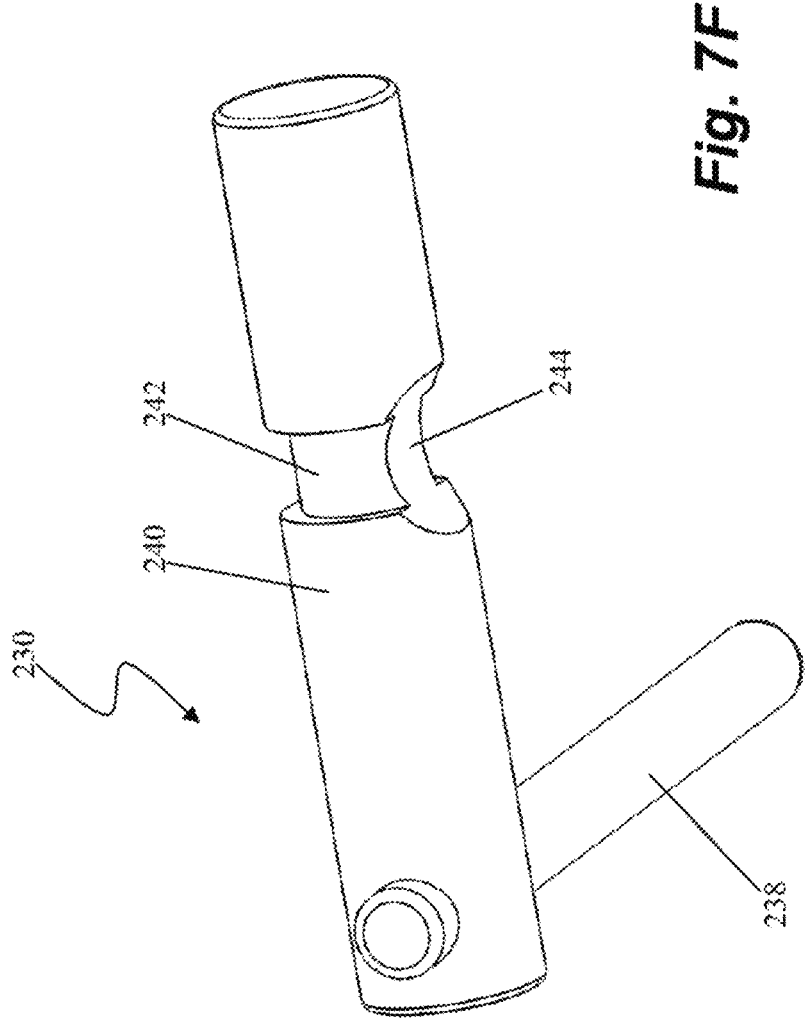

FIGS. 6A-6B depict device 100 with an insertion device 200 used to insert and expand device 100 within the disc space according to an embodiment. As will be described in more detail below, insertion device 200 generally includes a stabilizing component 204 and an expansion component 202. Expansion component 202 includes a knob 209 configured to be rotated to secure the expansion component 202 to intervertebral device 100 and a dial 208 configured to be rotated to expand intervertebral device 100, as discussed in more detail below. Stabilizing component 204 includes a handle 206 configured to be rotated to secure the component to device 100. FIGS. 7A-7E depict further detail regarding the components of insertion device 200.

Expansion component 202 includes a body 224, a shaft 222 extending from the body 224, a flange 226 at the distal end of shaft 222 and a distal threaded tip 228. Shaft 222 and body 224 include internal lumens that enable passage of shaft body 214 of stabilizing component 204 to pass through expansion component 202. Distal tip 228 is sized to be rotationally received by posterior or proximal threaded opening 126 of device. Flange 226 is wider than shaft 222 and threaded tip 228 to prevent expansion component 204 from being over-inserted when attached to expandable device 100. Knob 209 and dial 208 are selectively attachable to expansion component 202 via, for example, a rotational coupling with knob 209 and with a screw 220 for dial 208. Dial 208 can also include a threaded portion 221 configured to interface with a proximal threaded portion 212 of shaft 210. A lock 230 can be selectively insert into a lock aperture 232 through body 224 of expansion component 202 to lock rotation of stabilizing component 204 with respect to expansion component 202, as will be discussed in more detail below. Lock 230 can be selectively held in place with screw 234.

Stabilizing component 204 includes a shaft 210 extending from handle 206. Shaft 210 includes a proximal threaded portion 212 configured to interface with dial 208, a shaft body 214 configured to be extended through the expansion component 202, an implant extension 216 configured to extend through the implantable device 100 during implantation, and a threaded tip 218. Shaft 210 further includes a lock slot 236 configured to interface with lock 230.

Lock 230 includes a handle 238 and a lock body 240. Lock body 240 is configured to be inserted through lock aperture 232 in body 224 of stabilizing component 202. Lock body 240 further includes a recessed portion 242 having a reduced diameter that interfaces with the lock slot 236 in shaft body 214 of shaft 210. Recessed portion 242 of lock body 240 further includes a cutout 244 that allows for limited rotation of shaft body 214 when lock 230 is engaged with shaft 210.

Figure 8A:
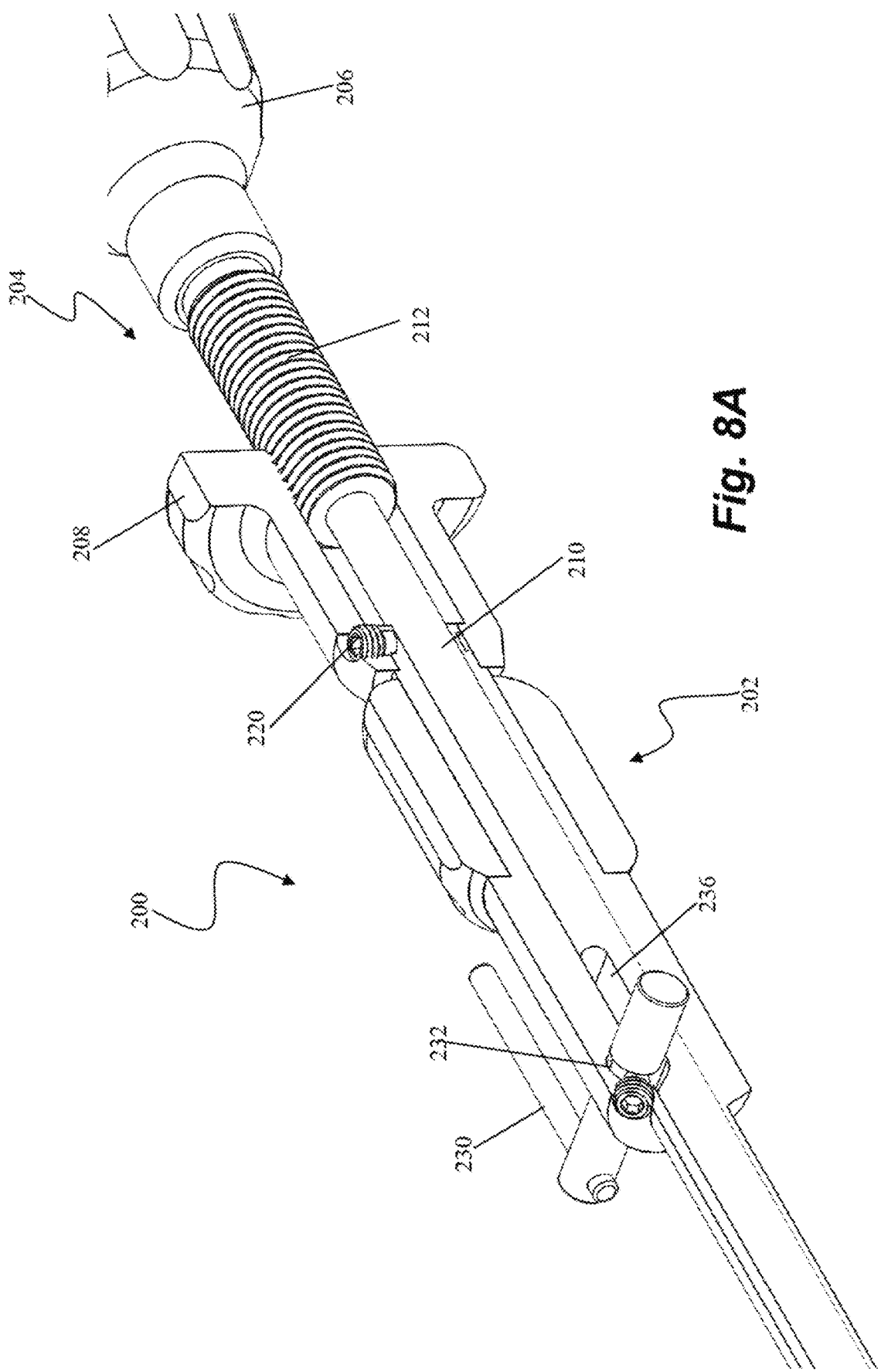
FIGS. 8A-8C depict portions of an insertion device for an expandable intervertebral body fusion device according to an embodiment.
Figure 8B:
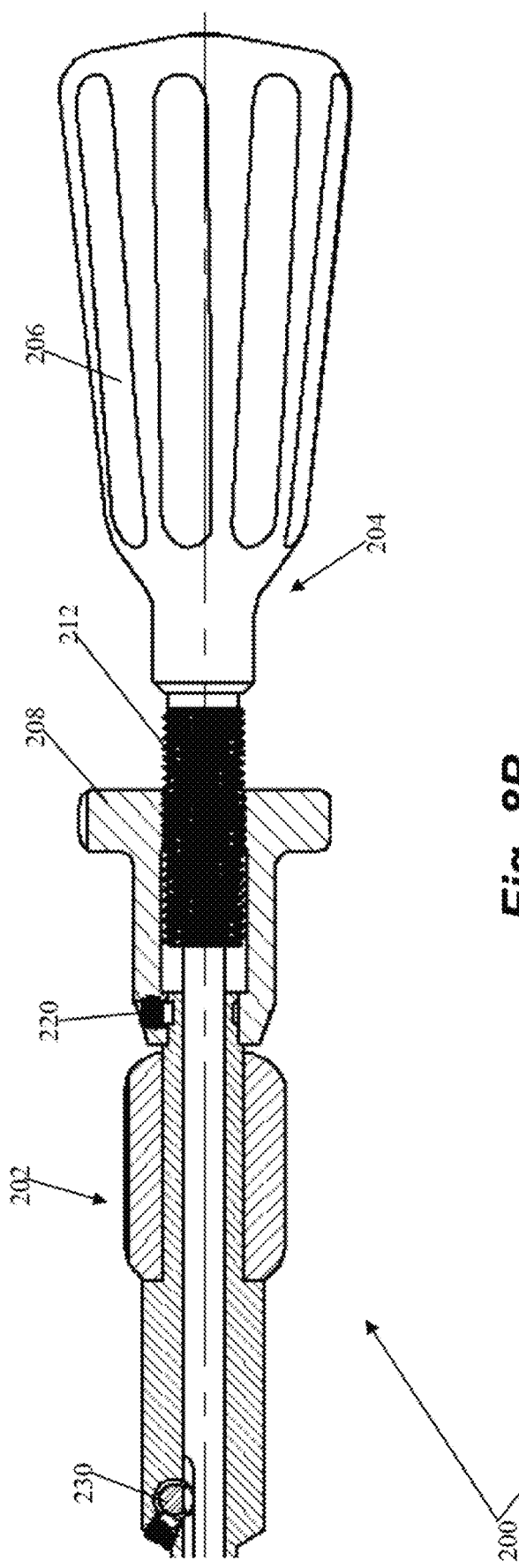
Figure 8C:
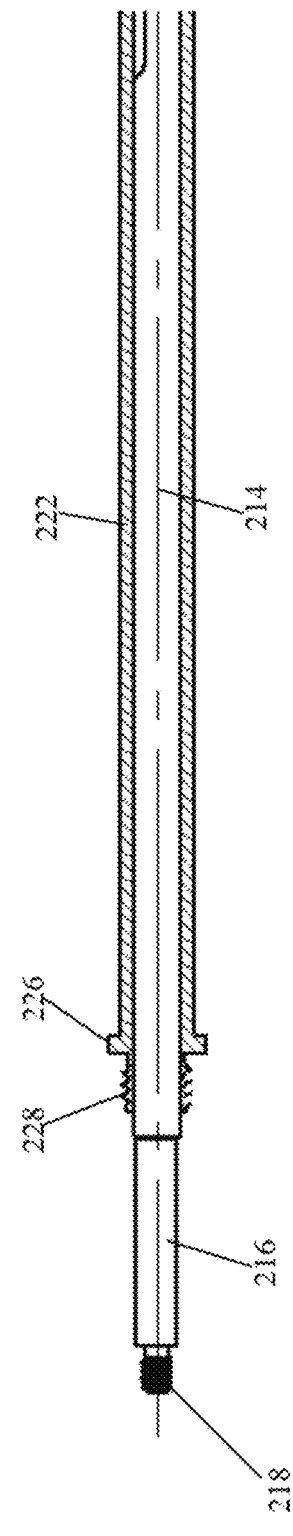

FIGS. 8A-8C further depict the interrelation of the components of inserter 200. Dial 208 is threaded onto proximal threaded portion 212 of stabilizing component 204. Shaft 210 of stabilizing component is inserted through expansion component 202 with implant extension 216 and threaded tip 218 extending distally from expansion component 202. Proximal end of expansion component 202 is secured to dial 208 with screw 220. Lock 230 can be selectively inserted into aperture 232 and through lock slot 236 in shaft 210.

FIGS. 9A-9I depict further details regarding the interaction between inserter 200 and expandable device 100. First, the distal tip 228 of the expansion component 202 is engaged with the posterior threaded opening 126 of implantable device 100 and the knob 209 is rotated to secure the tip 228 to the opening 126. If not already done so prior to attaching expansion component 202, stabilizing component 204 is inserted through stabilizing component 202 to the distal side of the expandable device 100. The implant extension 216 can be extended through the body of the implant 100 to engage the threaded tip 218 of the stabilizing component 204 to interface with the distal threaded opening 124 of the implant. Handle 206 can be rotated to secure the tip 218 to the opening 124. Lock 230 can now be inserted through slot 232 in expansion component and across slot 236 in shaft 214 of stabilizing component.

The dial 208 of the expansion component 202 can now be rotated to expand the implant 100 within the disc space. Dial 208 is rotated while the user holds the knob 209 such that the dial rotates relative to knob 209. Lock 230 prevents shaft 214 from rotating such that stabilizing component 204 maintains device 100 in a stable position. Dial 208 therefore rotates shaft 222 and distal tip 228 about shaft 214 of stabilizing component 204. This rotation pushes on the proximal or anterior end of device 100 while the distal or posterior end of the device is maintained stable, causing the distance between the anterior and posterior ends of the device to shorten and the device 100 to expand laterally outwardly. As described, above, device expands from the collapsed configuration shown in, e.g., FIGS. 1A, 5A and 6A, to the expanded configuration shown in, e.g., FIGS. 2A, 5B and 6B to cover a wider footprint in the disc space. Implant is therefore able to provide more robust and stable support in the disc space that is laterally wider than the access opening through which the implant is implanted.

Figure 9A:
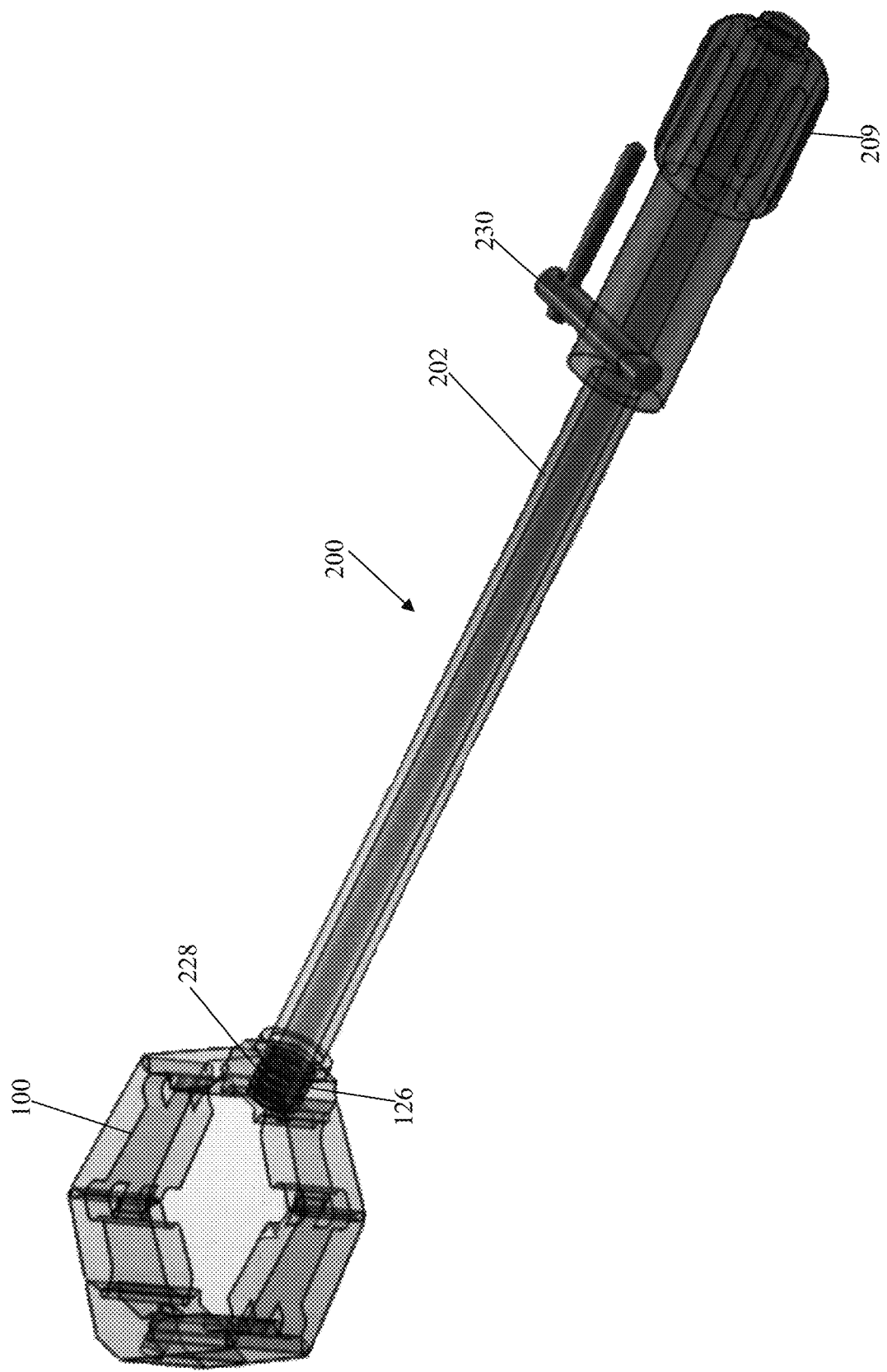
Figure 9B:
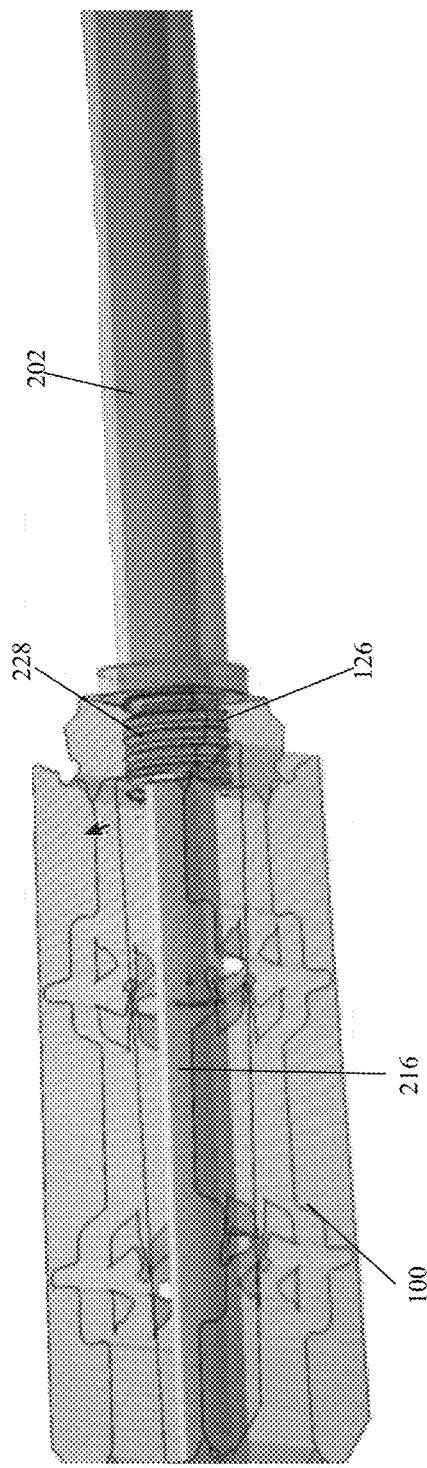
Figure 9C:
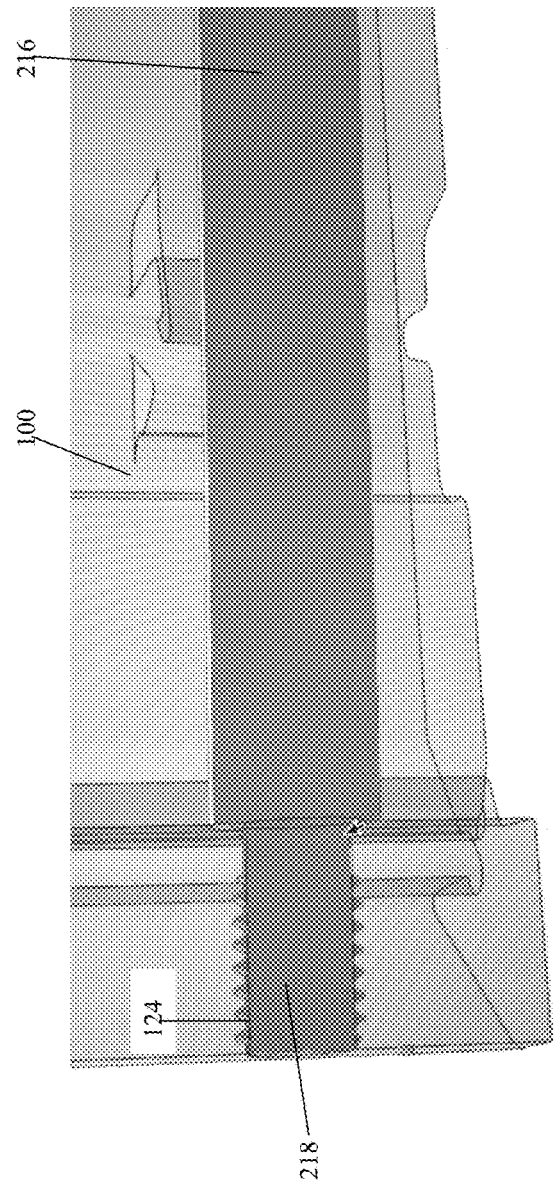
Figure 9D:
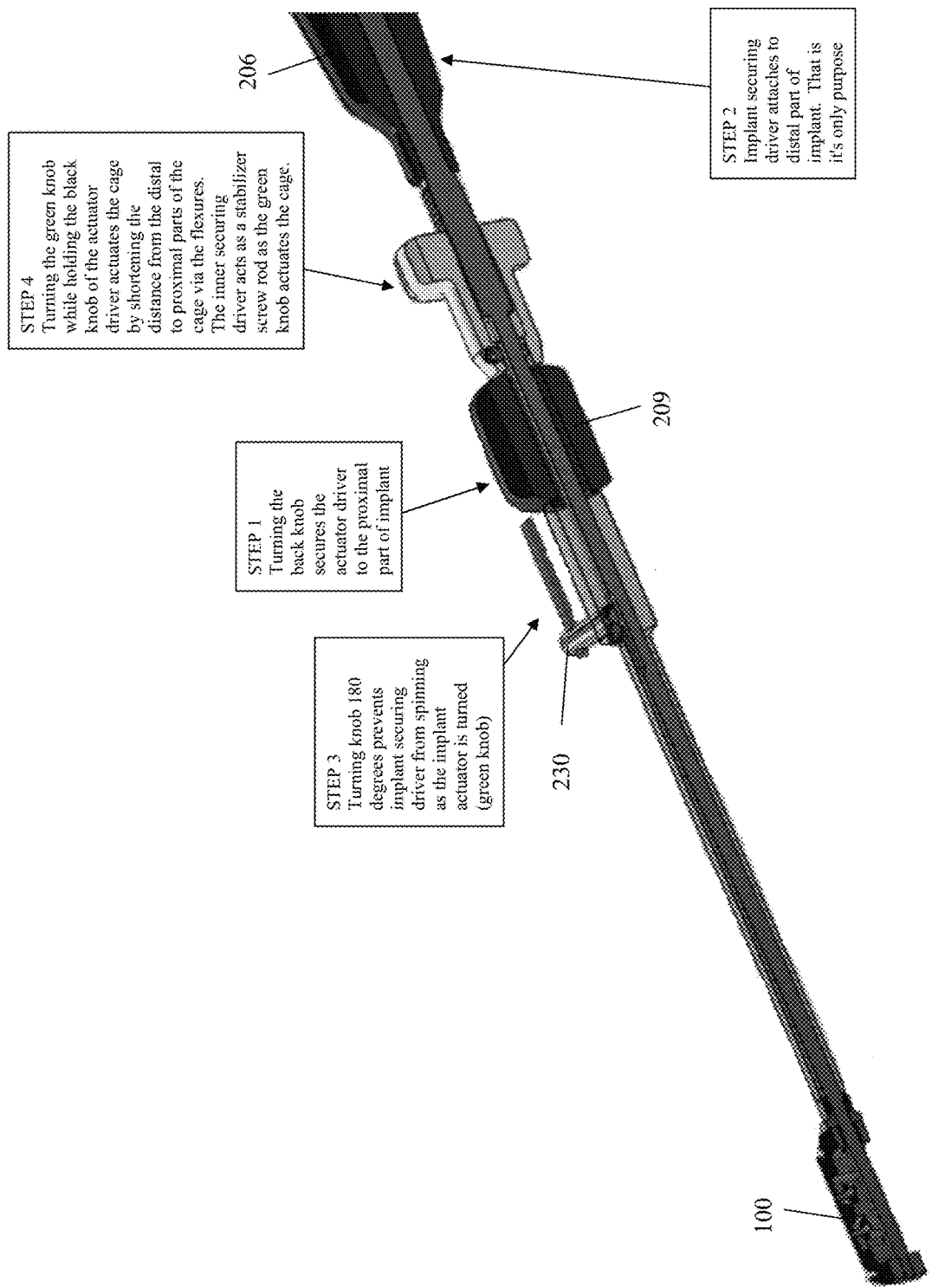
Figure 9G:
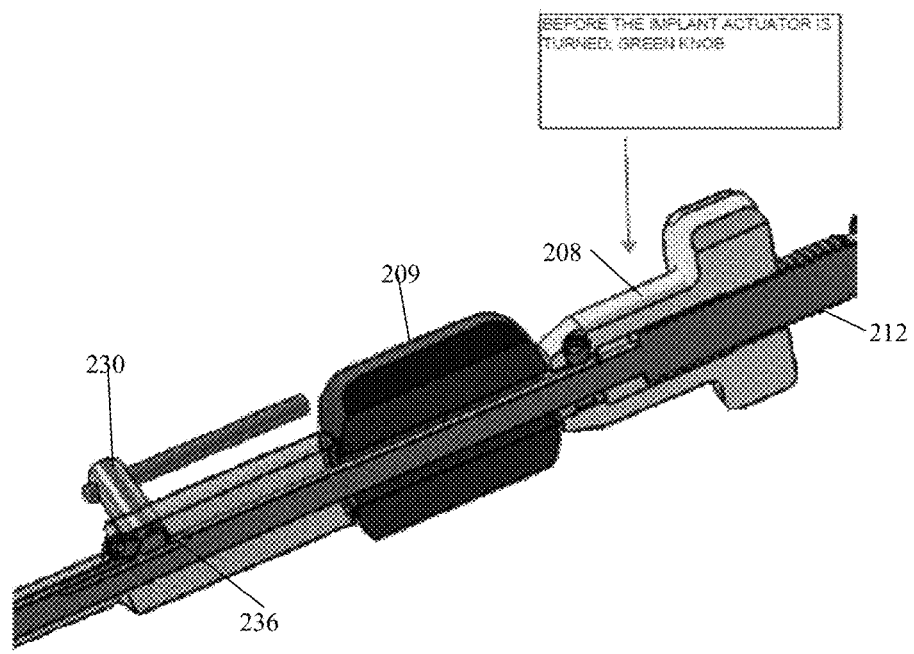
Figure 9H:
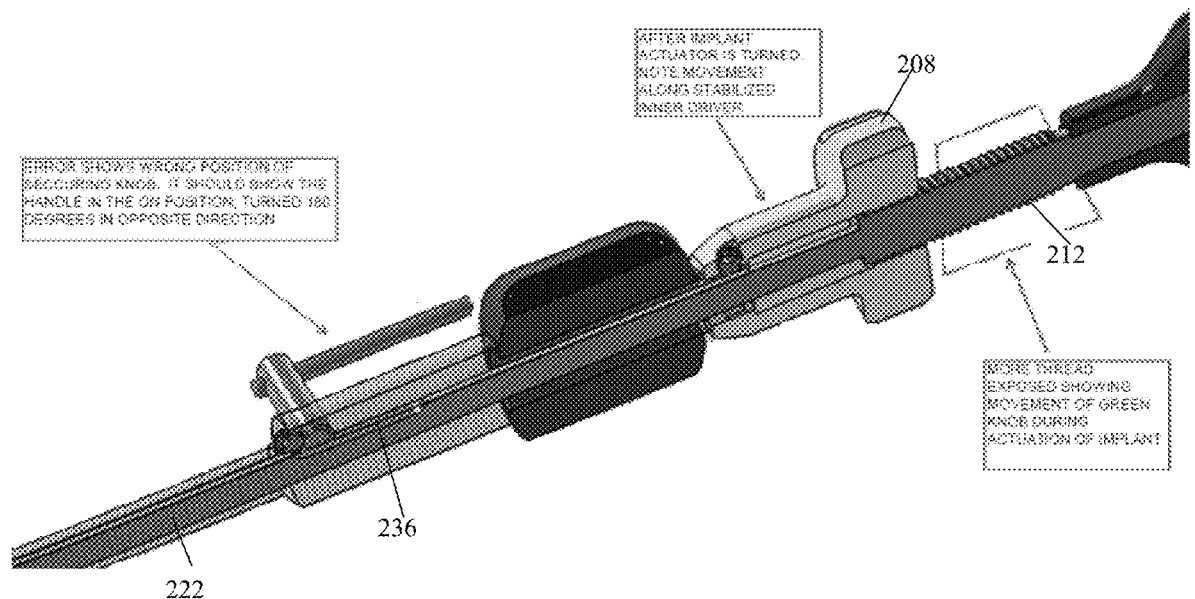

As can be seen in FIGS. 9E-9H, the slot 236 in shaft 210 of stabilizing component 204 can also serve to limit an amount that expansion component 202 can be rotated to expand device 100. Referring to FIGS. 9E and 9G, initially the lock 230 is positioned in at a proximal end of slot 236. As the dial 208 is rotated to rotate the shaft 222 to expand the device 100, the dial 208 travels linearly along the threaded portion 212 of the stabilizing component and the lock 230, which is inserted through a locking tube 231 of expansion component that enables shaft 222 to be rotated, is advanced linearly along slot 236. In the fully expanded position, as shown in FIG. 9H, the lock 230 abuts a distal end of the slot 236 such that further rotation of dial 208 with not cause any further linear advancement of shaft 222. The length of the slot 236 can be predetermined based on a desired or actual maximum expansion of the implanted device 100.

Figure 9I:
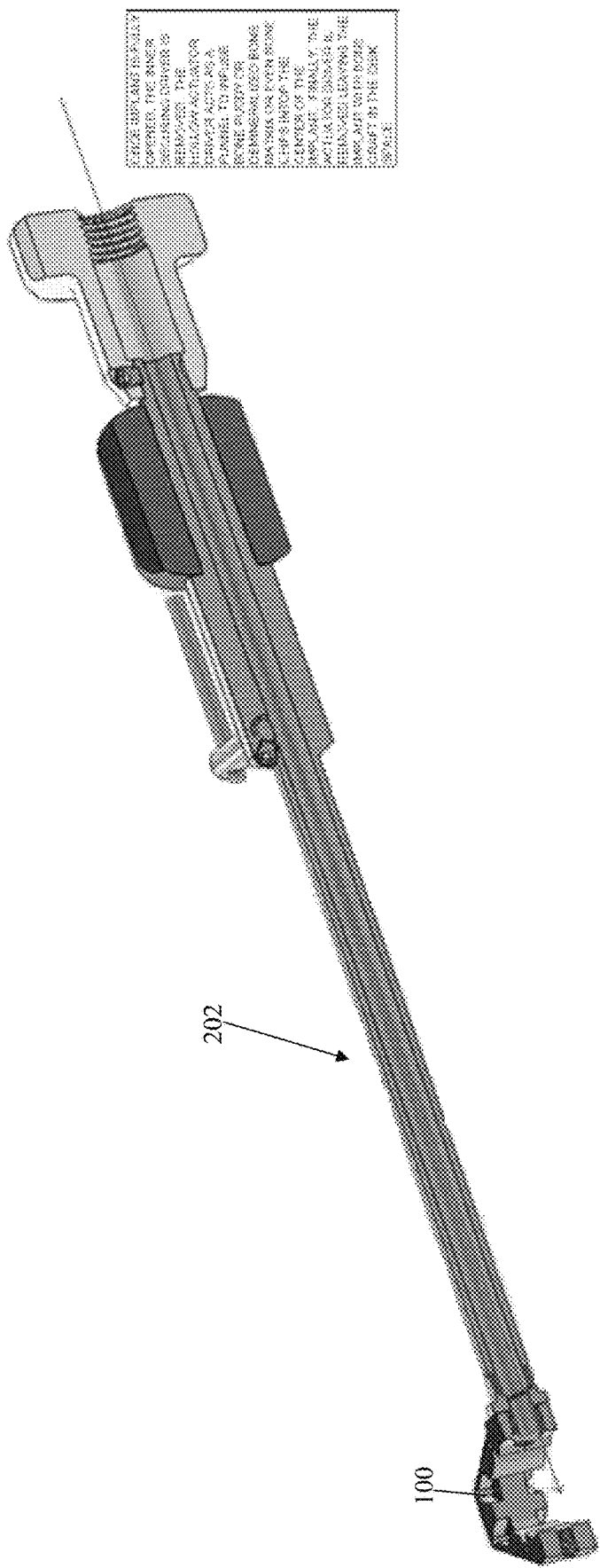
Figure 10A:
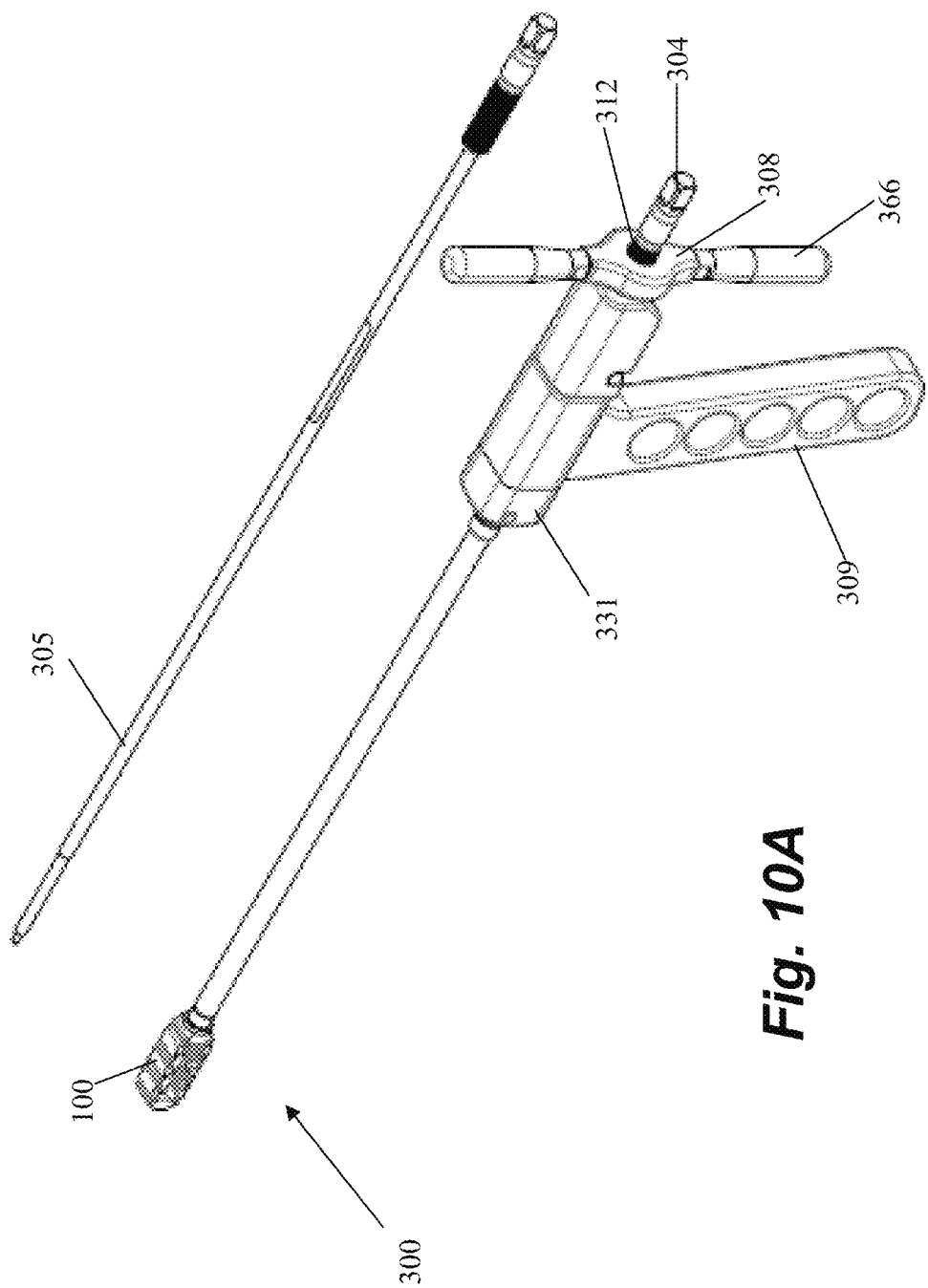
FIGS. 10A-10G depict portions of an insertion device for an expandable intervertebral body fusion device according to an embodiment.
Figure 10B:
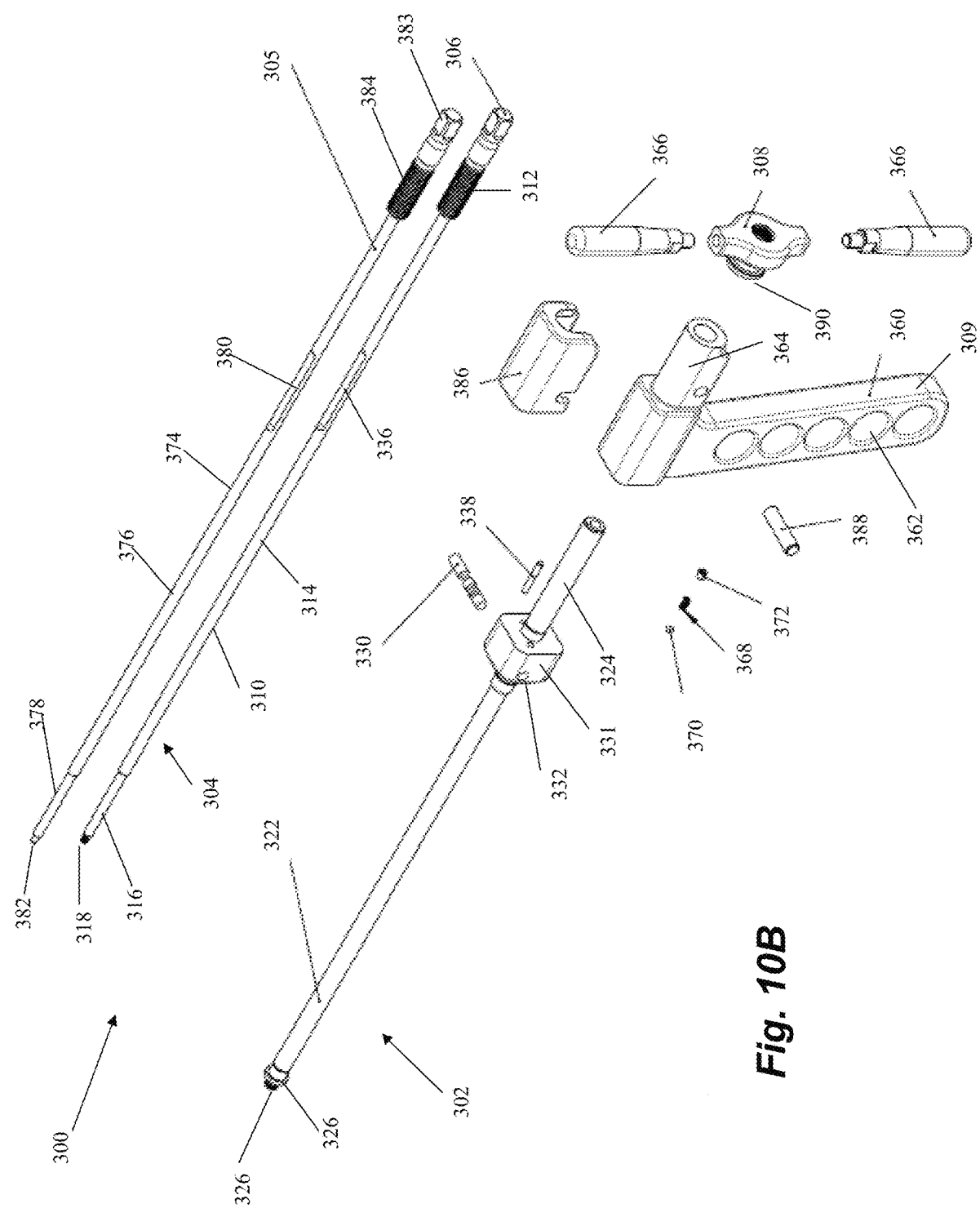
Figure 10C:
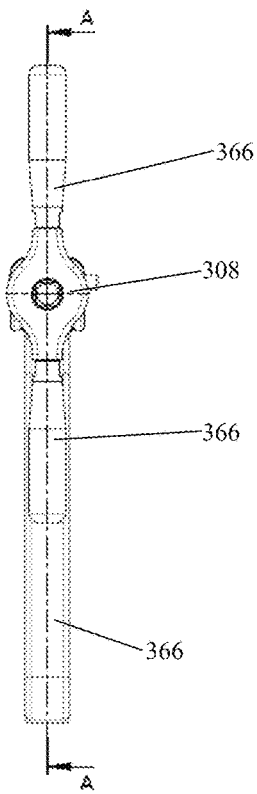
Figure 10D:
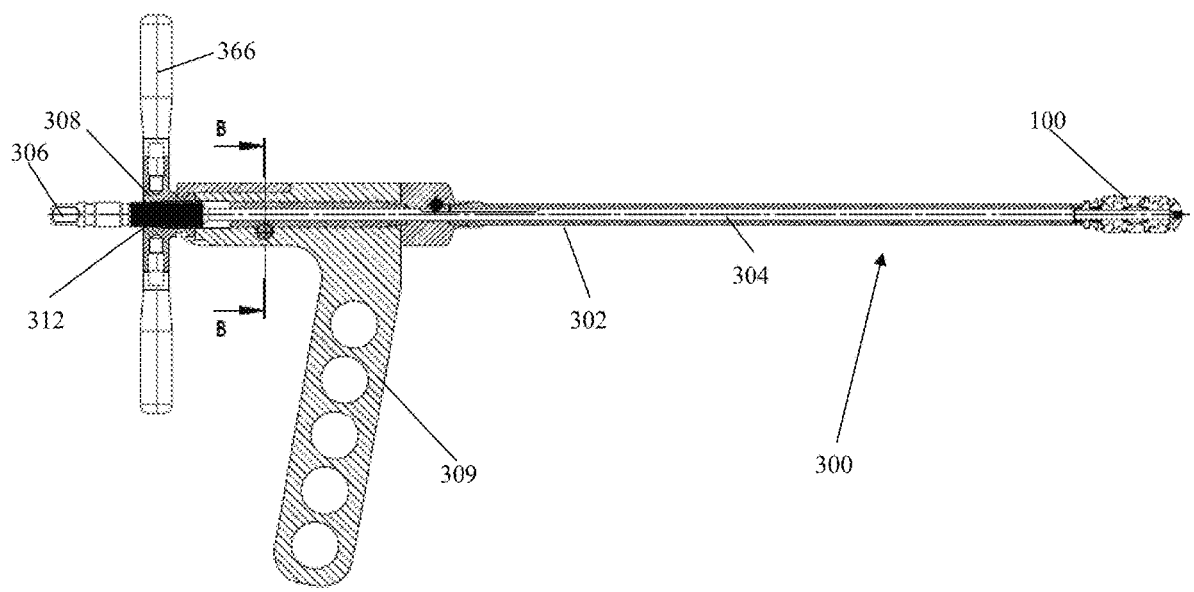
Figures 10E, 10F, 10G:
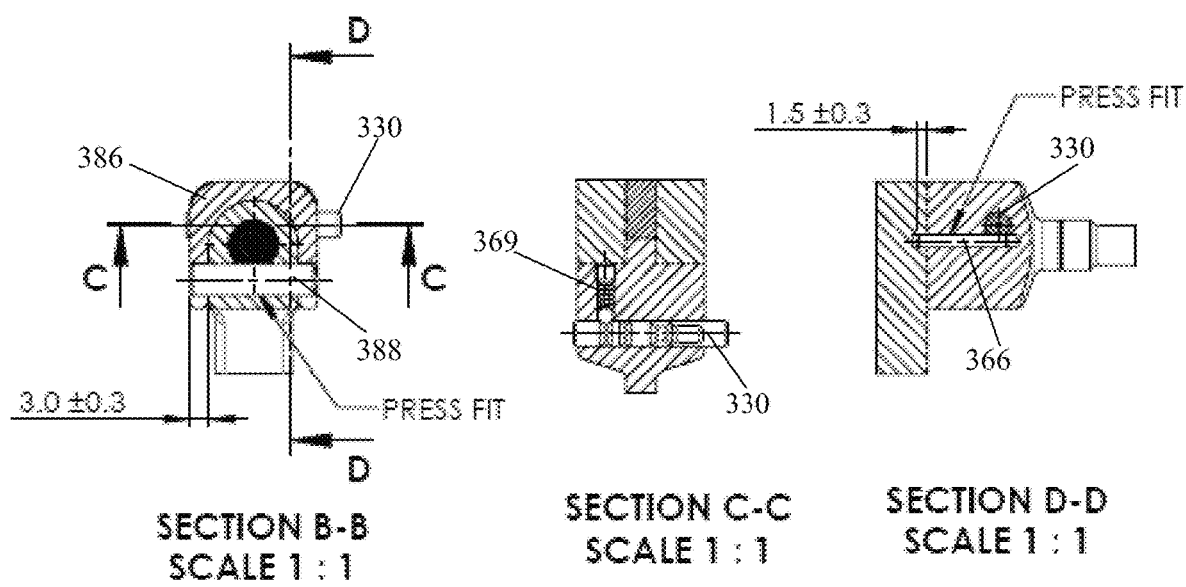

Referring to FIG. 9I, the stabilizing component 204 can be removed by rotating handle 206 to disengage the threaded tip 218 from the device and withdrawing the shaft 210 from the expansion component 202. The hollow expansion component 202 can then serve as a funnel to infuse one or more of, for example, bone putty, demineralized bone matrix, and bone chips into the now empty opening in the device 100 to aid the fusion process. Finally, the expansion component 202 can be disengaged from the implant 100 and removed, leaving the implant in the disc space with, e.g., bone graft in the interior of the device 100.

FIGS. 10A-10F depict an insertion device 300 for inserting and reversibly expanding and intervertebral body fusion device such as device 100 according to another embodiment. Insertion device 300 is substantially similar to insertion device 200 and includes a stabilizing component 302 and an expansion component 304. Insertion device 300 also includes an extraction component 305, as will be discussed in more detail below. Insertion device 300 can include any components described with respect to insertion device 200 and vice versa.

Expansion component 302 and includes a body 324, a shaft 322 extending from the body, a flange 326 at the distal end of shaft 322 and a threaded tip 328. Distal tip 328 is sized to be rotationally received by posterior or proximal threaded opening 126 of device 100 and flange 326 is wider than shaft 22 and threaded tip 328 to prevent expansion component 302 from being over-inserted when attached to expandable device 100. Expansion component 302 further includes a lock body 331 having a lock aperture 332 configured to receive a lock key 330 as described in more detail below.

Stabilizing component 304 includes a shaft 310 extending from a drive end 306. Shaft 312 includes a shaft body 314 configured to be inserted through a lumen in body 324 and shaft 322 of expansion component 302, an implant extension 316 configured to extend through the implantable device 100 during implantation, and a threaded tip 318. Shaft 310 further includes a lock slot 336 configured to interface with lock 330.

A handle 309 can include a grip 360 extending transversely with respect to the expansion and stabilizing shafts. Grip 360 can include finger apertures 362 for ergonomic reasons. A handle shaft 364 can include a lumen that enables insertion of the expansion component body 324 therethrough and that attaches to the lock body 331 of the expansion component 302. Actuation knob 308 can be attached to expansion component body 324 after insertion of body 324 through the lumen of handle shaft 364. Actuation knob 308 can include opposing expansion handles 366 that aid in providing additional torque for rotation of expansion component 302. Actuation knob 308 can also interface with a proximal threaded portion 312 of stabilizing shaft 310, such that rotation of actuation knob 308 causes the knob to travel along the threaded portion 312.

Lock 330 can include a lock handle 238 for rotating the lock between locked and unlocked positions when inserted through lock aperture 332 in body 324 of expansion component 302. Lock 330 can be removably retained in lock aperture 332 by lock retaining assembly 369 that utilizes the force of a spring 368 against a ball 370 that contacts lock and is inserted and biased against lock 330 with a nut 372. Ball 370 enables rotation of lock 330 between the locked and unlocked positions with lock handle 238. As with the previous embodiment, lock 330 can include a recessed portion having a reduced diameter that interfaces with the lock slot 236 in shaft body 214 of shaft 210. In the locked position, lock 330 functions to lock rotation of stabilizing component 204 with respect to expansion component 202. Further details regarding the positioning of lock 330 within device can be seen in FIG. 103-10G. As the expansion component 302 rotates about the locked stabilizing component 304, the lock 330 travels along the slot 336 in stabilizing shaft 310 as the actuation knob 308 travels along the threaded portion 312 of shaft 310. The slot 336 limits the distance that lock 330 can travel, thereby limiting to amount that device 100 can be expanded to a predetermined amount.

Because expansion component 302 is rotatably attached to implant 100, following expansion of implant expansion component cannot simply be rotated in the opposite direction to collapse the implant as such rotation instead causes the threaded tip 326 to disengage from the proximal opening of implant. Therefore, as noted above, insertion device 300 also includes an extraction component 305 that can be utilized to collapse the implant 100 for extraction. Similar to stabilizing component 304, extraction component 305 includes a shaft 374 extending from a drive end 383, with the shaft including a shaft body 376 configured to be inserted through expansion component 302, an implant extension 378, a lock slot 380 and a distal tip 382. Extraction component 305 also includes a proximal threaded portion 384 along which actuation knob 308 can travel.

Extraction component 305 differs from stabilizing component 304 primarily in that distal tip 382 is not threaded. Otherwise, the components of extraction component 305 generally are configured and function the same as those of stabilizing component 304. In the case of lock slot 380, the extraction component 305 is not locked from rotating when the implant 100 is collapsed, but if it is desirable to employ lock 330 with extraction component the lock slot 380 would function similarly to the lock slot 336 of stabilizing component 304. A shoe 386 can be releasably held on handle shaft 364 with dowel pin 388 and engage lip 390 of actuation knob 308 when stabilizing component 305 is used to prevent rotation of actuation knob 308. Rotation of extraction component 305 with a suitable driver with the actuation knob 308 locked from rotating by shoe 386, with the non-threaded distal dip 382 able to rotate within the distal opening of the implant 100, pulls the expansion component 302 back along the proximal threaded portion 384 as the extraction component 305 is rotated. This proximal force pulling back on the implant 100 disengages the flexure-based latches on the implant to collapse the device 100 and enable the device to be extracted from the disc space. In an embodiment, extraction component 305 can be rotated with a driver that includes outwardly extending handles similar to handles 366 employed with actuation knob 308 to provide for greater torque.

In use, expansion component 302 is connected to implant 100 by rotating the component to secure threaded tip 326 to implant 100 and expansion body 324 is inserted through handle shaft 364 with lock body 331 secured to handle shaft 364. Stabilizing component 304 can then be inserted through the lumen of expansion body 324 to extend implant extension 316 and threaded tip 318 of stabilizing component 304 beyond the distal end of the expansion component and threaded tip can be screwed into the implant with a socket driver attached to drive end 306. Lock 330 can then be inserted into lock aperture 332 to prevent additional rotation of stabilizing component 304. Once the implant 100 is properly positioned within the body, actuation knob 308 can be rotated with the aid of handles 366 providing additional torque to rotate expansion component 302 to expand the implant 100. As the component is rotated, the actuation knob 308 travels along proximal threaded portion 312 of stabilizing component 304 and lock 330 travels with respect to lock slot 336, with the distal end of lock slot 336 provided a maximum limit on the amount of expansion. The expansion component 302 can then be disconnected from the implant, the lock 330 removed and the stabilizing component 304 rotated to be disconnected from the device. The inserter 300 is then removed with the implant 100 remaining in the body.

If it becomes desirable to remove the implant 100, either during the procedure or at a later time, extraction component 305 is employed. After securing expansion component 302 to the device, extraction component 305 is inserted through the expansion component and the distal, non-threaded tip 382 inserted into the distal opening of the implant 100 with a press fit. The shoe 386 is then secured to the handle shaft 364 with dowel pin 388 with the shoe 386 engaging the inner lip 390 of the actuation knob 308 to prevent rotation of the actuation knob. The extraction component 305 can then be rotated clockwise to enable the actuation knob 308 to travel proximally back along the threaded portion 384 of extraction component 305 pull on the implant 100 with expansion component 302 to disengage the flexure-based latches on the implant to collapse the device 100. Implant 100 can then be extracted from the intervertebral disc space, or repositioned and again expanded.

The typical height opening after a discectomy available to insert the implant can be from 4-14 mm depending on how collapsed the disc space is. One would need disc space distractors either a mechanical device or a lollipop sizer to expand the disc space. The typical width of the surgical path into the disc space after retracting the nerve root could be 10-12 mm. Through a transforaminal interbody approach (TLIF: transforaminal interbody fusion) where you remove the superior and inferior facet you may be able to get an additional 1-2 mm more of working room.

In another embodiment, device can be inserted into the disc space and expanded vertically to expand the disc space, with the flexures locking the device at the expanded height and maintaining the expanded disc space.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A system comprising an expandable intervertebral body fusion device having a distal opening and a proximal opening and an insertion device for inserting and expanding the expandable intervertebral body fusion device into an intervertebral disc space defined between adjacent vertebrae of a patient, comprising:
    a stabilizing shaft having a stabilizing tip and
    configured to be rotated to engage the stabilizing tip with the distal opening of the expandable intervertebral body fusion device;
    an expansion shaft having an expansion tip, the expansion shaft having an internal lumen enabling passage of the stabilizing shaft and the stabilizing tip through the expansion shaft and distally beyond the expansion tip, the expansion shaft
    configured to be rotated to engage the expansion tip with the proximal opening of the expandable intervertebral body fusion device;
    a shaft lock configured to selectively lock the stabilizing shaft to prevent rotation of the stabilizing shaft while enabling rotation of the expansion shaft; and
    an actuation handle configured to rotate the expansion shaft, wherein rotation of the actuation handle when the shaft lock has locked the stabilizing shaft causes the expansion shaft to be advanced in an axial direction relative to the stabilizing shaft to press a proximal portion of the expandable intervertebral body fusion device towards a distal portion of the expandable intervertebral body fusion device to cause the expandable intervertebral body fusion device to expand in a direction transverse to the axial direction.

2. The system of claim 1, wherein the stabilizing shaft includes a threaded exterior along a proximal portion of the stabilizing shaft, and wherein rotation of the actuation handle to advance the expansion shaft in an axial direction relative to the stabilizing shaft causes the actuation handle to travel along the threaded exterior of the stabilizing shaft in the axial direction.

3. The system of claim 1, wherein the shaft lock is configured to engage an axial slot in the stabilizing shaft such that rotation of the actuation handle advances the shaft lock in the axial direction along the axial slot.

4. The system of claim 3, wherein a length of the axial slot corresponds with a maximum distance that the expansion shaft can be advanced in the axial direction relative to the stabilizing shaft.

5. The system of claim 1, wherein the stabilizing shaft is selectively removable from within the lumen of the expansion shaft.

6. The system of claim 5, wherein the lumen of the expansion shaft is configured to enable of insertion of bone growth material through the expansion shaft to the expandable intervertebral body fusion device when the stabilizing shaft is not within the lumen of the expansion shaft.

7. The system of claim 1, wherein the stabilizing tip and the expansion tip are threaded.

8. The system of claim 1, wherein the actuation handle includes a rotatable dial.

9. The system of claim 8, wherein the rotatable dial includes a cylindrical body and one or more engagement features extending outwardly from the cylindrical body and configured to be gripped by a user to rotate the rotatable dial.

10. The system of claim 1, further comprising an extraction component having an extraction shaft and a non-threaded distal tip configured to engage the distal portion of the expandable intervertebral body fusion device.

11. A system comprising an expandable intervertebral body fusion device having a distal opening and a proximal opening and an insertion device for inserting and expanding the expandable intervertebral body fusion device into an intervertebral disc space defined between adjacent vertebrae of a patient, comprising:
    a stabilizing shaft having a stabilizing tip configured to engage the distal opening of the expandable intervertebral body fusion device;
    an expansion shaft having an expansion tip configured to engage the proximal opening of the expandable intervertebral body fusion device; and wherein the expansion shaft includes an internal lumen enabling passage of the stabilizing shaft and the stabilizing tip through the expansion shaft and distally beyond the expansion tip;
    a shaft lock configured selectively lock the stabilizing shaft to prevent rotation of the stabilizing shaft while enabling rotation of the expansion shaft; and
    an actuation handle configured to rotate the expansion shaft, wherein rotation of the actuation handle when the shaft lock has locked the stabilizing shaft causes the expansion shaft to be advanced in an axial direction relative to the stabilizing shaft to press a proximal portion of the expandable intervertebral body fusion device towards a distal portion of the expandable intervertebral body fusion device to cause the expandable intervertebral body fusion device to expand in a direction transverse to the axial direction.

12. The system of claim 11, wherein the stabilizing shaft includes a threaded exterior along a proximal portion of the stabilizing shaft, and wherein rotation of the actuation handle to advance the expansion shaft in an axial direction relative to the stabilizing shaft causes the actuation handle to travel along the threaded exterior of the stabilizing shaft in the axial direction.

13. The system of claim 11, wherein the shaft lock is configured to engage an axial slot in the stabilizing shaft such that rotation of the actuation handle advances the shaft lock in the axial direction along the axial slot.

14. The system of claim 13, where a length of the axial slot corresponds with a maximum distance that the expansion shaft can be advanced in the axial direction relative to the stabilizing shaft.

15. The system of claim 11, wherein the stabilizing shaft is selectively removable from within the lumen of the expansion shaft.

16. The system of claim 15, wherein the lumen of the expansion shaft is configured to enable of insertion of bone growth material through the expansion shaft to the expandable intervertebral body fusion device when the stabilizing shaft is not within the lumen of the expansion shaft.

17. The system of claim 11, wherein the stabilizing tip and the expansion tip are threaded.

18. The system of claim 11, wherein the actuation handle includes a rotatable dial.

19. The system of claim 18, wherein the rotatable dial includes a cylindrical body and one or more engagement features extending outwardly from the cylindrical body and configured to be gripped by a user to rotate the rotatable dial.

20. The system of claim 11, further comprising an extraction shaft having a non-threaded distal tip configured to engage the distal portion of the expandable intervertebral body fusion device.

\* \* \* \* \*